US012636101B2

(12) United States Patent
Evalekar et al.

(10) Patent No.: US 12,636,101 B2
(45) Date of Patent: May 26, 2026

(54) SYSTEM AND METHOD FOR AUTOMATED DETERMINATION OF ROBOT BASE LOCATION VIA TROCAR'S ACCESSIBILITY MAP

(71) Applicant: EDDA TECHNOLOGY, INC., Princeton, NJ (US)

(72) Inventors: Yash Evalekar, Princeton, NJ (US); Yuanfeng Mao, Princeton, NJ (US); Guo-Qing Wei, Plainsboro, NJ (US); Li Fan, Belle Mead, NJ (US); Xiaolan Zeng, Princeton, NJ (US); Jianzhong Qian, Princeton Junction, NJ (US)

(73) Assignee: EDDA TECHNOLOGY, INC., Princeton, NJ (US)

( * ) Notice: Subject to any disclaimer, the term of this patent is extended or adjusted under 35 U.S.C. 154(b) by 515 days.

(21) Appl. No.: 18/163,665

(22) Filed: Feb. 2, 2023

(65) Prior Publication Data

US 2024/0261045 A1     Aug. 8, 2024

(51) Int. Cl.
  B25J 9/16      (2006.01)
  A61B 34/32     (2016.01)
  (Continued)

(52) U.S. Cl.
  CPC ............. A61B 34/32 (2016.02); B25J 9/1669 (2013.01); B25J 9/1679 (2013.01); G16H 40/63 (2018.01); A61B 2034/107 (2016.02)

(58) Field of Classification Search
  CPC .............. A61B 34/32; A61B 2034/107; A61B 2034/105; A61B 34/20; A61B 34/30;
  (Continued)

(56) References Cited

U.S. PATENT DOCUMENTS 6,728,599 B2    4/2004  Wang et al.
10,973,597 B2   4/2021  Mccormick et al.
      (Continued)

FOREIGN PATENT DOCUMENTS

KR        1049507 B1    7/2011
WO     2022119754 A1    6/2022

OTHER PUBLICATIONS

Notice of Allowance mailed Mar. 21, 2025 in U.S. Appl. No. 18/163,703.

(Continued)

*Primary Examiner* — Bao Long T Nguyen
(74) *Attorney, Agent, or Firm* — Venable LLP

(57)          ABSTRACT

The present teaching relates to automated robot base location determination. An instrument access map is obtained with respect to a surgical instrument for performing a surgical operation on an organ and defines a surface area on the organ with cut points that form a surgery trajectory. Information about a robot and a surgical environment is received and used to generate a robot access map with multiple robot base locations. The robot is for controlling the surgical instrument to perform the surgical operation along the surgery trajectory. A robot base location is selected based on evaluation parameters derived for each of the robot base locations. Control signals are generated for configuring the robot at the selected robot base location to facilitate the surgical operation.

18 Claims, 25 Drawing Sheets

(51) Int. Cl.
     *G16H 40/63*          (2018.01)
     *A61B 34/10*          (2016.01)

(58) Field of Classification Search
     CPC ....... A61B 34/37; B25J 9/1669; B25J 9/1679;
                                        B25J 9/1664; G16H 40/63
     See application file for complete search history.

(56)                    References Cited

U.S. PATENT DOCUMENTS

| | | | |
|---|---|---|---|
| 2010/0234857 A1 | 9/2010 | Itkowitz et al. | |
| 2011/0146676 A1 | 6/2011 | Dallam et al. | |
| 2011/0306986 A1 | 12/2011 | Lee et al. | |
| 2014/0227132 A1 | 8/2014 | Neister | |
| 2014/0378995 A1 | 12/2014 | Kumar et al. | |
| 2017/0042730 A1 | 2/2017 | He et al. | |
| 2019/0343589 A1 | 11/2019 | Kim et al. | |
| 2020/0113635 A1 | 4/2020 | Ida et al. | |
| 2020/0383734 A1 | 12/2020 | Dahdouh | |
| 2021/0068908 A1 | 3/2021 | Thienphrapa et al. | |
| 2021/0196384 A1 | 7/2021 | Shelton, IV et al. | |
| 2021/0315637 A1 | 10/2021 | Ida et al. | |
| 2021/0378752 A1 | 12/2021 | Paul et al. | |
| 2022/0000557 A1 | 1/2022 | Dehghani | |
| 2022/0104822 A1 | 4/2022 | Shelton, IV et al. | |
| 2022/0331022 A1 | 10/2022 | Troxell et al. | |
| 2022/0361968 A1* | 11/2022 | Noonan ................. | A61B 34/37 |
| 2022/0370139 A1 | 11/2022 | Kaouk et al. | |
| 2022/0378524 A1 | 12/2022 | Schreiber et al. | |
| 2022/0406452 A1 | 12/2022 | Shelton, IV | |
| 2023/0020476 A1 | 1/2023 | Junio et al. | |
| 2023/0317258 A1 | 10/2023 | Brown et al. | |
| 2023/0346493 A1 | 11/2023 | Hallen | |
| 2024/0261028 A1 | 8/2024 | Evalekar et al. | |
| 2024/0261038 A1 | 8/2024 | Evalekar et al. | |
| 2024/0261045 A1 | 8/2024 | Evalekar et al. | |

OTHER PUBLICATIONS

International Search Report and Written Opinion mailed May 14, 2025 in International Patent Application No. PCT/US2025/019528.
International Search Report and Written Opinion mailed on May 17, 2024 in International Patent Application No. PCT/US2024/014171.
International Search Report and Written Opinion mailed on May 20, 2024 in International Patent Application No. PCT/US2024/014179.
Sundaram et al., "Task-specific robot base pose optimization for robot-assisted surgeries." Frontiers in Robotics and AI, Biomedical Robotics, Dec. 2, 2022, pp. 1-17, Institute of Robotics and Mechatronics, German Aerospace Center (DLR), Wessling, Germany.
International Search Report and Written Opinion mailed on May 23, 2024 in International Patent Application No. PCT/US2024/014178.
Mountney et al., "Three-Dimensional Tissue Deformation Recovery and Tracking", Introducing techniques bsed on laparoscopic or endoscopic images, IEEE Signal Processing Magazine, Jun. 14, 2010, pp. 14-24, vol. 27, Issue 4, IEEE Xplore.
Joerger et al., "Global Laparoscopy Positioning System with a Smart Trocar", Proceedings—2017 IEEE 17th International Conference on Bioinformatics and Bioengineering, Oct. 23, 2017-Oct. 25, 2017, pp. 359-366, IEEE Computer Society, United States of America.
Selha et al., "Dexterity optimization by port placement in robot-assisted minimally invasive surgery", 2001 SPIE International Symposium on Intelligent Systems and Advanced Manufacturing, Oct. 28, 2001-Oct. 31, 2001, pp. 1-8, Newton, MA, United States of America.
Hayashi et al., "Optimal port placement planning method for laparoscopic gastrectomy", Abstract, International Journal of Computer Assisted Radiology and Surgery, Mar. 7, 2017, 1 Page, vol. 12, Springer, United States of America.
Hussain et al., "Development of Simulator for Robot Assisted Surgical Platform for Cholecystectomy Training", Proc. of the 2019 IEEE International Conference on Signal and Image Processing Applications (IEEE ICSIPA 2019), Sep. 17-19, 2019, pp. 1-5, IEEE Xplore.
Laribi et al., "A design of slave surgical robot based on motion capture", Proceedings of the 2012 IEEE International Conference on Robotics and Biomimetics, Dec. 11-14, 2012, pp. 600-605, IEEE Xplore.
Vitiello et al., "Emerging Robotic Platforms for Minimally Invasive Surgery", IEEE Reviews in Biomedical Engineering, Mar. 29, 2013, pp. 111-126, vol. 6, IEEE.
Yip et al., "A Vision-Assisted Semi-Automatic Uterus Manipulation Approach Based on a Pose Estimating Trocar", Proceedings of the 2019 IEEE/ASME International Conference on Advanced Intelligent Mechatronics, Jul. 8-12, 2019, pp. 169-174, IEEE Xplore.
Notice of Allowance mailed Nov. 5, 2024 in U.S. Appl. No. 18/163,686.

* cited by examiner

Cannula 210

Trocar point 220

Skin surface 230

Accessibility map 240

Target organ 250

Marked cutting points 260

Determine candidate trocar locations 605

Generate accessibility map for each candidate location 615

Determine evaluation para. for each location 625

Access optimization models trained 635

Select an optimized trocar location via models 645

Output optimized trocar location 655

Determine operating space via input trocar locations <u>705</u>

Determine resolution used for optimizing robot base loc. <u>715</u>

Generate operating space grid for evaluation <u>725</u>

Determine evaluation para. for each grid unit <u>735</u>

Select an optimized robot Base loc. via models <u>745</u>

Output the optimized Robot base location <u>755</u>

| Ins. Loc. | Base Grid | D(I, B) | Ins. Loc. E-parameters | Base Grid E-parameters | - - - - - - - - - - |
|-----------|-----------|---------|------------------------|------------------------|--------------------|

Fig. 9B

| W1 | W2 | W3 | W4 ........... Wi | Wi+1 ....... Wm | Wm | Wm+1 ....... Wn |
|----|----|----|------------------|-----------------|-----|-----------------|

Fig. 9C

Receive trocar/robot combo feature matrix 1140

Processing matrix info (e.g., normalization, etc.) 1150

Send processed feature matrix to ANN models 1160

Receive output from ANN models on best combo 1170

Output the best combo from the ANN models 180

SYSTEM AND METHOD FOR AUTOMATED DETERMINATION OF ROBOT BASE LOCATION VIA TROCAR'S ACCESSIBILITY MAP

CROSS REFERENCE TO RELATED APPLICATIONS

The present application is related to U.S. patent application Ser. No. 18/163,686, filed on Feb. 2, 2023, and U.S. patent application Ser. No. 18/163,703, filed on Feb. 2, 2023, the contents of which are hereby incorporated by reference in their entireties.

BACKGROUND

1. Technical Field

The present teaching generally relates to computers. More specifically, the present teaching relates to signal processing.

2. Technical Background

Robotics in the past few decades have been deployed in different situations, including in industrial settings such as robots on assembly lines that assemble products 24/7 and in other types of settings such as transporting goods in a warehouse or assisting surgeons in different types of surgical operations. For example, robotic surgery has been widely accepted in liver resection surgeries due to robots' incomparable precision, reachability, and flexibility in tasks that may be more difficult for humans to do. Additional benefits a surgical robot brings is the fact that its performance does not degrade over time as compared with a human who gets tired, needs to eat, and sleep, and can be distracted.

In a robot assisted surgery, a robot may be deployed to work with doctors or nurses to perform certain specified actions and may be positioned at a certain location in the surgery room. Conventionally, the placement of a robot in the surgery room is done by a human manually based on, e.g., experience of a good location in the room related to what is to be done by the robot, a location of a tool to be handled by the robot, and the nature of the action, etc. Given that, if it turned out that the placement of the robot is not appropriate, it has to be moved during the surgery, which is problematic.

Thus, there is a need to develop solutions that address the shortcomings of the current state of the art.

SUMMARY

The teachings disclosed herein relate to methods, systems, and programming for information management. More particularly, the present teaching relates to methods, systems, and programming related to hash table and storage management using the same.

In one example, a method, implemented on a machine having at least one processor, storage, and a communication platform capable of connecting to a network for automated robot base location determination. An instrument access map is obtained with respect to a surgical instrument for performing a surgical operation on an organ and defines a surface area on the organ with cut points that form a surgery trajectory. Information about a robot and a surgical environment is received and used to generate a robot access map with multiple robot base locations. The robot is for controlling the surgical instrument to perform the surgical operation along the surgery trajectory. A robot base location is selected based on evaluation parameters derived for each of the robot base locations. Control signals are generated for configuring the robot at the selected robot base location to facilitate the surgical operation.

In a different example, a system is disclosed for automated robot base location determination. The system includes a robot base location optimizer that is implemented by a processor and configured for selecting a robot base location. An instrument access map is obtained with respect to a surgical instrument for performing a surgical operation on an organ and defines a surface area on the organ with cut points that form a surgery trajectory. Information about a robot and a surgical environment is received and used to generate a robot access map with multiple robot base locations. The robot is for controlling the surgical instrument to perform the surgical operation along the surgery trajectory. A robot base location is selected based on evaluation parameters derived for each of the robot base locations. Control signals are generated for configuring the robot at the selected robot base location to facilitate the surgical operation.

Other concepts relate to software for implementing the present teaching. A software product, in accordance with this concept, includes at least one machine-readable non-transitory medium and information carried by the medium. The information carried by the medium may be executable program code data, parameters in association with the executable program code, and/or information related to a user, a request, content, or other additional information.

Another example is a machine-readable, non-transitory and tangible medium having information recorded thereon for automated robot base location determination. The information, when read by the machine, causes the machine to perform various steps. An instrument access map is obtained with respect to a surgical instrument for performing a surgical operation on an organ and defines a surface area on the organ with cut points that form a surgery trajectory. Information about a robot and a surgical environment is received and used to generate a robot access map with multiple robot base locations. The robot is for controlling the surgical instrument to perform the surgical operation along the surgery trajectory. A robot base location is selected based on evaluation parameters derived for each of the robot base locations. Control signals are generated for configuring the robot at the selected robot base location to facilitate the surgical operation.

Additional advantages and novel features will be set forth in part in the description which follows, and in part will become apparent to those skilled in the art upon examination of the following and the accompanying drawings or may be learned by production or operation of the examples. The advantages of the present teachings may be realized and attained by practice or use of various aspects of the methodologies, instrumentalities and combinations set forth in the detailed examples discussed below.

BRIEF DESCRIPTION OF THE DRAWINGS

The methods, systems and/or programming described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 9B illustrates an exemplary feature vector for each pair of trocar and robot base locations, in accordance with an embodiment of the present teaching;

FIG. 9C illustrates an exemplary weight vector with weights therein corresponding to respective features in a feature vector, in accordance with an embodiment of the present teaching;

DETAILED DESCRIPTION

Figure 1:
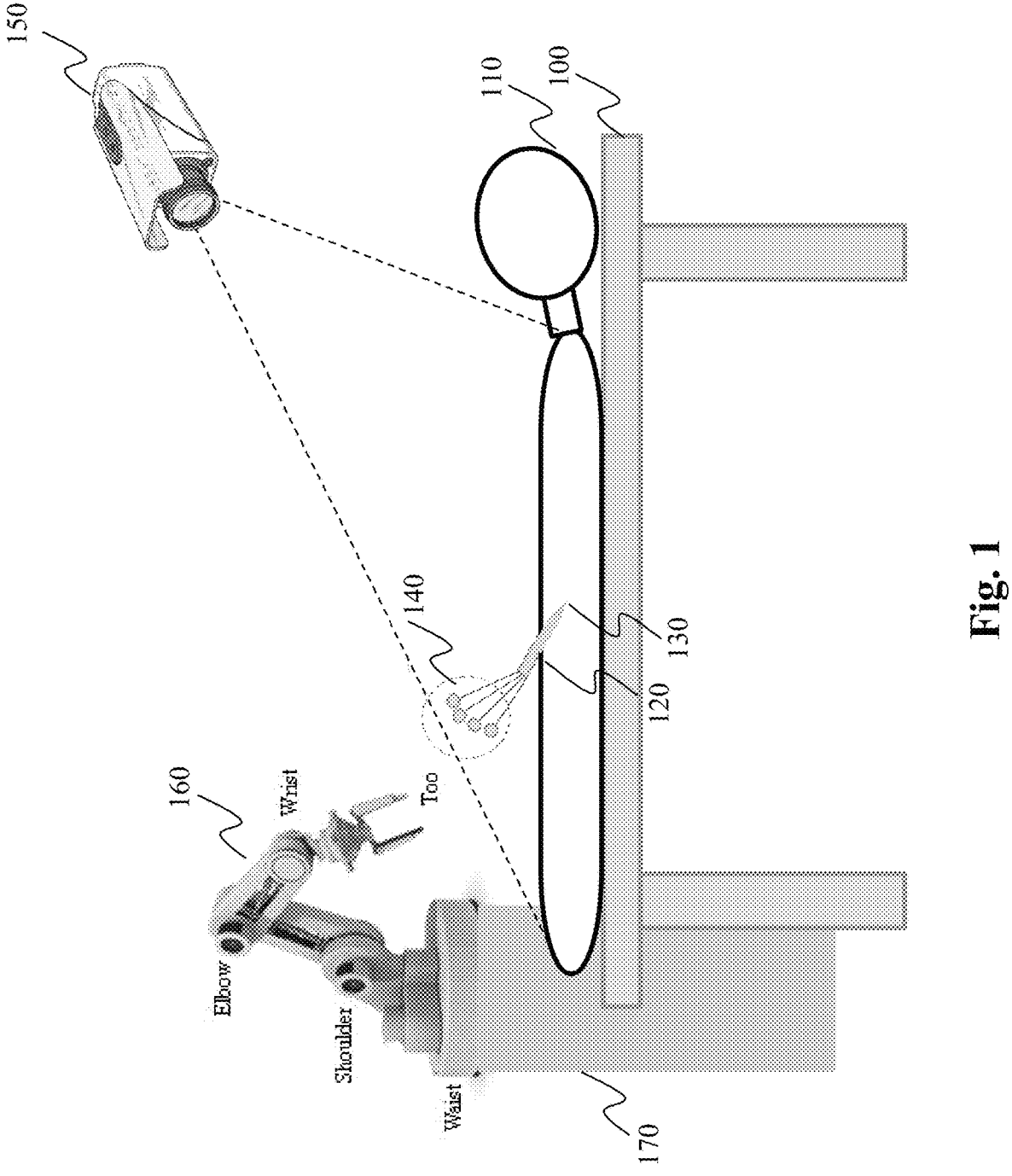
FIG. 1 shows a surgical setting in which a robot is deployed to handle some aspects of a surgery.

In the following detailed description, numerous specific details are set forth by way of examples in order to facilitate a thorough understanding of the relevant teachings. However, it should be apparent to those skilled in the art that the present teachings may be practiced without such details. In other instances, well known methods, procedures, components, and/or system have been described at a relatively high-level, without detail, in order to avoid unnecessarily obscuring aspects of the present teachings.

The present teaching discloses exemplary methods, systems, and implementations for automatic optimization of surgical instrument insertion location and robot base location, either separately or in combination. In a robot-assisted surgery environment, it may include a robot deployed to perform certain functions during the surgery and some surgical instrument inserted into the body of a patient for performing some intended operation. The insertion of the instrument may be made at different locations on the skin of the patient to reach the target location on an organ where the operation is to be performed. The surgical instrument may be inserted at a so-called trocar point on the skin. Different trocar points may impact the performance of the operation. For example, depending on the position of an organ to be operated and the precise cut position to remove a portion of the organ, some trocar points may cause collision with other anatomical structure while others may not.

When a robot is deployed in a surgical environment, it may be used to assist some actions, e.g., controlling the surgical instrument to move to a specified target position on the organ such as a cut point on an organ. To do so, the robot may be positioned at a base location from where it can be accordingly configured to execute the intended function. The base location of the robot may also impact what it does and, hence, the quality of the surgery. For example, when the arm of the robot becomes too extended to reach the surgical instrument, its performance may be risky. Certain base location of the robot may make its operation too close to its singularity (a position where the robot can get stuck for to inoperable situation due to, e.g., mechanical limitation). Therefore, both the insertion location of a surgical instrument (trocar point) and the robot's base location may be selected to avoid issues in operation. The present teaching discloses method and systems that automatically optimize a selected insertion location of the surgical instrument as well as a base location of the robot to minimize risks of the robot-assisted surgery.

The optimization according to the present teaching is directed to determination of either or both of an insertion location for a surgical instrument and a base location for a robot. With respect to trocar point optimization, candidate trocar locations may be assessed based on different criteria. Examples include the goal of the underlying surgery (e.g., resection of a liver), the scope of the surgery (e.g., how many lobes on the liver to be removed), the role of the instrument plays in a surgery (e.g., a surgical instrument with a cutter at the tip to make cuts on an organ), the spatial configuration between the surgical instrument and the target organ, and the potential collisions between the insertion location and the target organ positions. Candidate robot base locations may also be assessed based on some criteria, e.g., the function(s) the robot is expected to perform (e.g., to move a surgical instrument to various specified 3D coordinates in the workspace), the kinematic configurations to enable the robot to perform the required functions, spatial relationship between the robot and the surgical instrument, proximity to robot's singularity, or whether the robot at a candidate base location may interfere other equipment in the surgery room, etc. Depending on specific applications, the criteria used to assess each candidate insertion location and based location may differ.

In some embodiments of the present teaching, the trocar position and the base location are optimized sequentially, i.e., one is optimized first and then the other is subsequently optimized with respect to the optimized result of the first. For example, the trocar position may be optimized first. Once the insertion location of the surgical instrument is obtained, the base location of the robot is then optimized with respect to the optimized insertion location of the surgical instrument. On the other hand, it is also possible to optimize the base location of the robot first and then the trocar position for the surgical instrument may then be optimized with respect to the already fixed robot base location.

In some embodiments of the present teaching, the trocar position of the surgical instrument and the base location of the robot may be optimized simultaneously. That is, what is optimized is the combination of the two locations, one for insertion of the surgical instrument and one for where the robot is located in the workspace. In optimizing the combination, a feature vector may be obtained for each possible pair of the locations to create a matrix with each row for a candidate pair and columns for the feature values of the feature vector for the candidate pair. In some implementation, a best combination may be selected as optimized result based on assessment scores associated with the candidate pairs. In some embodiments, an assessment score for a candidate pair may be determined based on a weighted sum of all feature values of the corresponding feature vector. Weights for different features in a feature vector may be learned via machine learning based on training data from past surgeries and performance evaluation results. In this optimization scheme, a best combination of an insertion location and a base location may correspond one that yields a maximum assessment score or a highest weighted sum.

In some embodiments, instead of optimizing the combination by selecting, one of the discrete weighted sums for individual combinations, a model base approach may be applied. A model may be represented by embedded model parameters and its embeddings may be learned via machine learning based on training data collected from historic data related to surgery room configurations with assessment on performance of the associated surgeries. The assessment may be presented as vectors, scores, etc. and may include various parameters designed to measure success of a medical operation. Examples of such parameters include, e.g., whether adjustments were made during the surgery to either trocar point of robot's base location, the length of the surgery, rate of incidents during the surgery (e.g., whether the surgical instrument accidentally collided with other anatomical structure, surgeon's satisfaction about the setting, patient's recovery time, etc.). Such ground truth may be used for training so that the trained embeddings incorporate knowledge related to what configuration of surgical instrument insertion location and robot base locations that that work well in different types of surgeries and settings. Details of different aspects of the present teaching and various embodiments are disclosed below with reference to different figures.

FIG. 1 shows a workspace in a surgical setting in which a robot 160 is deployed to handle some aspects of a surgery. In this workspace, there is a surgical table 100, a patient 110 on the surgical table with a surgical instrument 120 inserted therein with a rigid body having a tip 130. A tracking mechanism is deployed in the workspace with a sensor, e.g., a camera 150 that is configured to be able to monitor tracking devices 140 attached to one end of the surgical instrument 120 that is outside of the patient's body. Assume that the sensor 150 is calibrated in the workspace, when it observes the tracking devices, the tracking mechanism may determine the 3D coordinate of the surgical instrument in a coordinate system defined with respect to the workspace. As the surgical instrument is a rigid body (including the body 120 and the tip portion 130), through the detection of the tracking devices, the 3D coordinate of the tip 130 of the surgical instrument may also be accordingly determined.

In this exemplary surgical setting, the robot 160 may have a base 170 so that the robot may be moved around by moving the base 170 to different locations. A surgical robot may be deployed to, e.g., handle some aspects of the operation in a surgery. For instance, robot 160 may be used to control the movement of the surgical instrument 120 in a manner so that the tip 130 of the instrument reaches some specified 3D coordinate in the workspace, e.g., a particular cut point on an organ of the patient. Such control may be achieved by configuring the kinematic parameters of the robot so that it can control the instrument to travel along a path from a current location of tip 130 to the specified 3D coordinate. Depending on the base location of robot 160, the robot needs to be configured differently to achieve the goal. As discussed herein, some base locations may yield better or more convenient performance and some may not.

Figure 2:
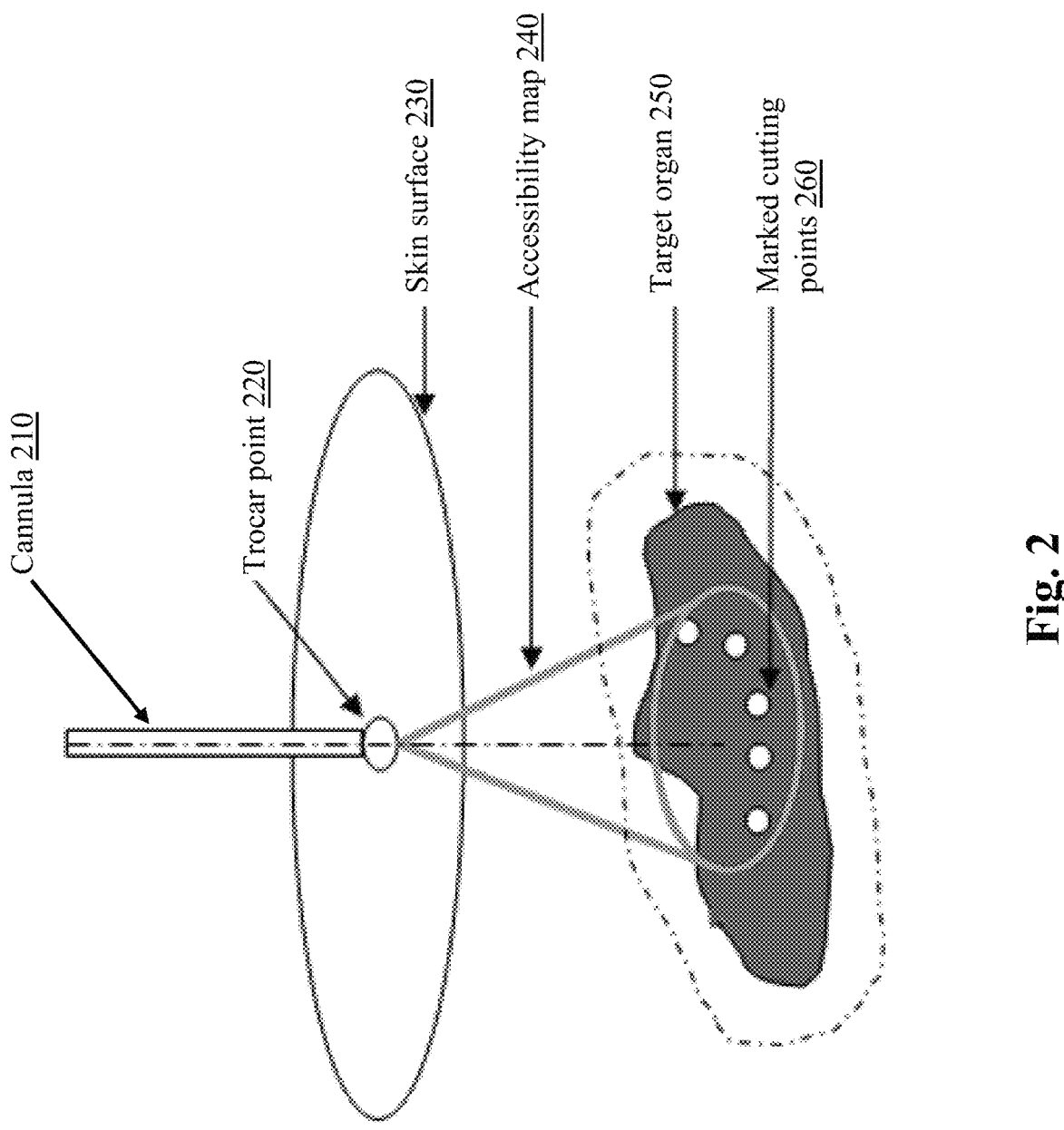
FIG. 2 shows a surgical instrument inserted into a patient's body via a trocar point that yields a corresponding access map over an organ to be operated on, in accordance with an embodiment of the present teaching.

The configuration needed to enable robot 160 to perform desired function may differ with respect to the insertion location or trocar point of the surgical instrument on the skin of the patient. The location of the trocar point is also important from the standpoint of its accessibility to various target points. For example, the surgical instrument 120 may be used to resect a portion of an organ so that the tip of the surgical instrument has to reach a series of cut points on the organ from the trocar point. FIG. 2 shows a surgical instrument, i.e., a cannula 210, inserted into a patient's skin 230 via a trocar point 220 that yields a corresponding access map 240 over a target organ 250 to be operated on. To operate on the target organ, a series of cut points may be preplanned prior to the surgery, as shown in FIG. 2 as marked cut points 260. To ensure that the cannula 210 is able to reach all the preplanned cut points in 260, the access map 240 associated with the trocar point 220 has to enclose all the cut points. Thus, a minimum condition for determining a trocar point may be that the access map associated with the trocar point has to have all cut points included therein.

Figure 3A:
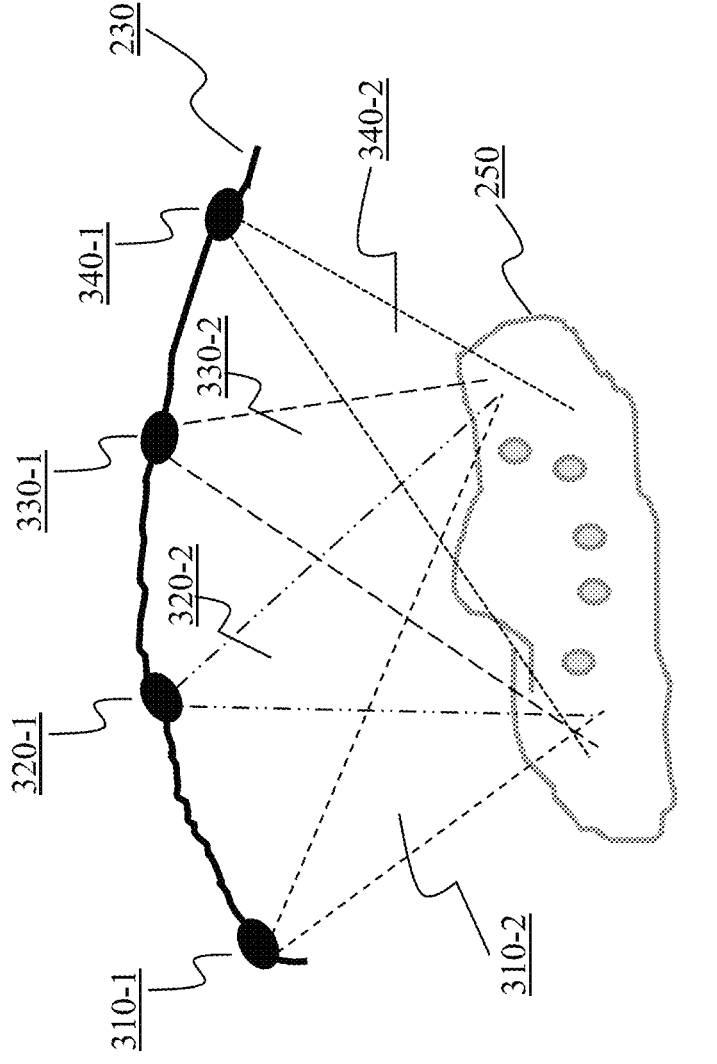
FIG. 3A illustrates that different maneuvers are needed to enable a surgical instrument inserted from different trocar locations to reach an area on an organ, in accordance with an embodiment of the present teaching.

There are often more than one trocar point locations that meet this minimum condition. However, to reach the cut points, the surgical instrument inserted from different trocar points may reach the cut points via different paths, some of which may be more problematic than others. For instance, from a certain trocar point, the surgical instrument may collide with other anatomical structures before reaching the cut points and may need to get around to avoid collision, making it more difficult and less efficient. FIG. 3A illustrates that although multiple trocar points 310-1, 320-1, 330-1, and 340-1 all yield satisfactory access maps 310-2, 320-2, 330-2, and 340-2 to cover preplanned cut points on organ 250, the surgical instrument inserted at different trocar points has to maneuver differently to access each of the cut points. For example, as trocar point 310-1 and 340-1 have a longer distance to some of the cut points, it is more likely that the surgical instrument may encounter other anatomical structures. In addition, from these trocar points, the tip of the surgical instrument may not be able to cut the organ at the cut point in a direction that is substantially perpendicular to the surface of the organ, making it more likely to have undesirable performance in the operation. As such, a determination is needed to select a trocar point that is appropriate or optimal given different considerations.

Figure 3B:
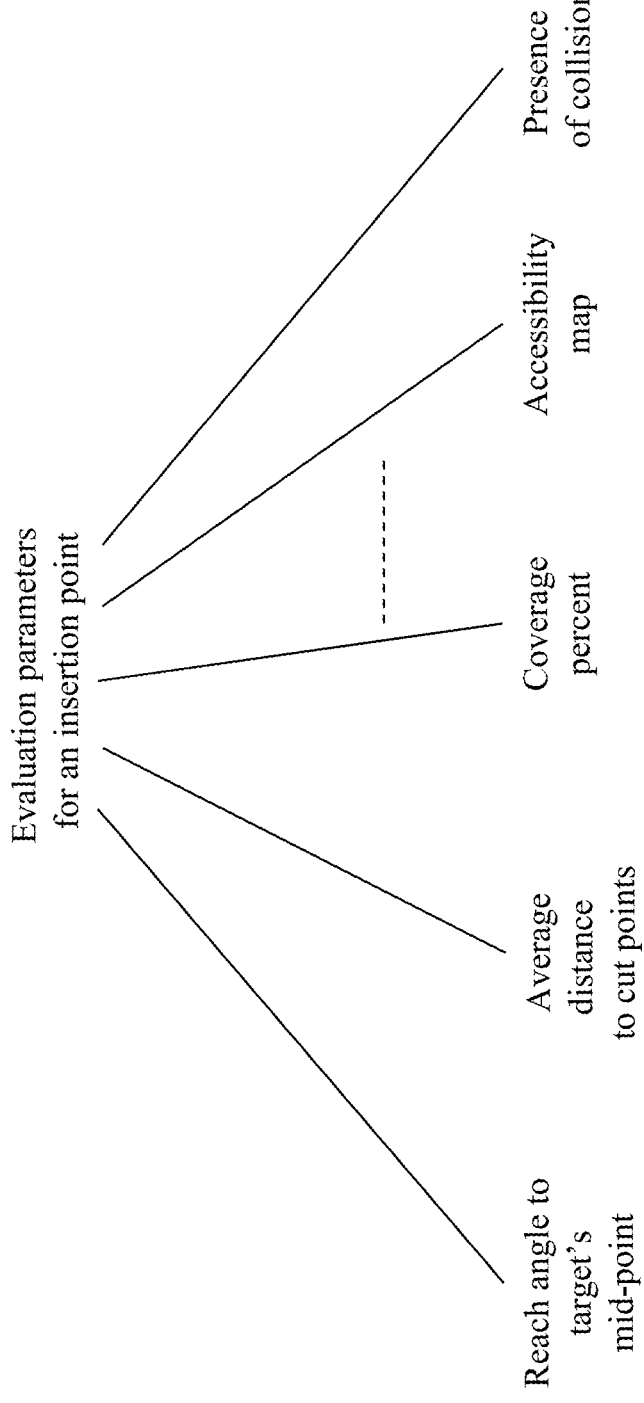
FIG. 3B illustrates different considerations in evaluating a candidate trocar point, in accordance with an embodiment of the present teaching.

FIG. 3B illustrates exemplary considerations in evaluating each trocar point, in accordance with an embodiment of the present teaching. As illustrated, the considerations may include an average distance to the cut points, an angle to reach a selected cut point (e.g., a mid-point of the cut points), a percent of cut points included in an access map, . . . , whether collision exists with respect to other objects, and whether there is any collision in reaching the cut points. Additional or different evaluation criteria may also be used. As can be seen in FIG. 3A, a trocar point that is not directly above a target organ may have a higher average distance to reach the cut points and may have a more slanted angle with respect to, e.g., the average surface norm of the target organ and, hence, to the cut points. The more slanted the angle a trocar point has, the more likely that the surgical instrument inserted from the trocar point may collide with other anatomical structures along paths to reach different cut points. In addition, with a trocar point further away from a target organ, it is also more likely that its access map may not cover some of the cut points, whether it is due to collision or a too large of a distance for the surgical instrument to reach some of the cut points. Given that, not only it is important to select candidate trocar points that yield access maps that can cover all cut points but also essential to select one that is most viable in terms of risk free, efficiency, and operability.

Figure 4A:
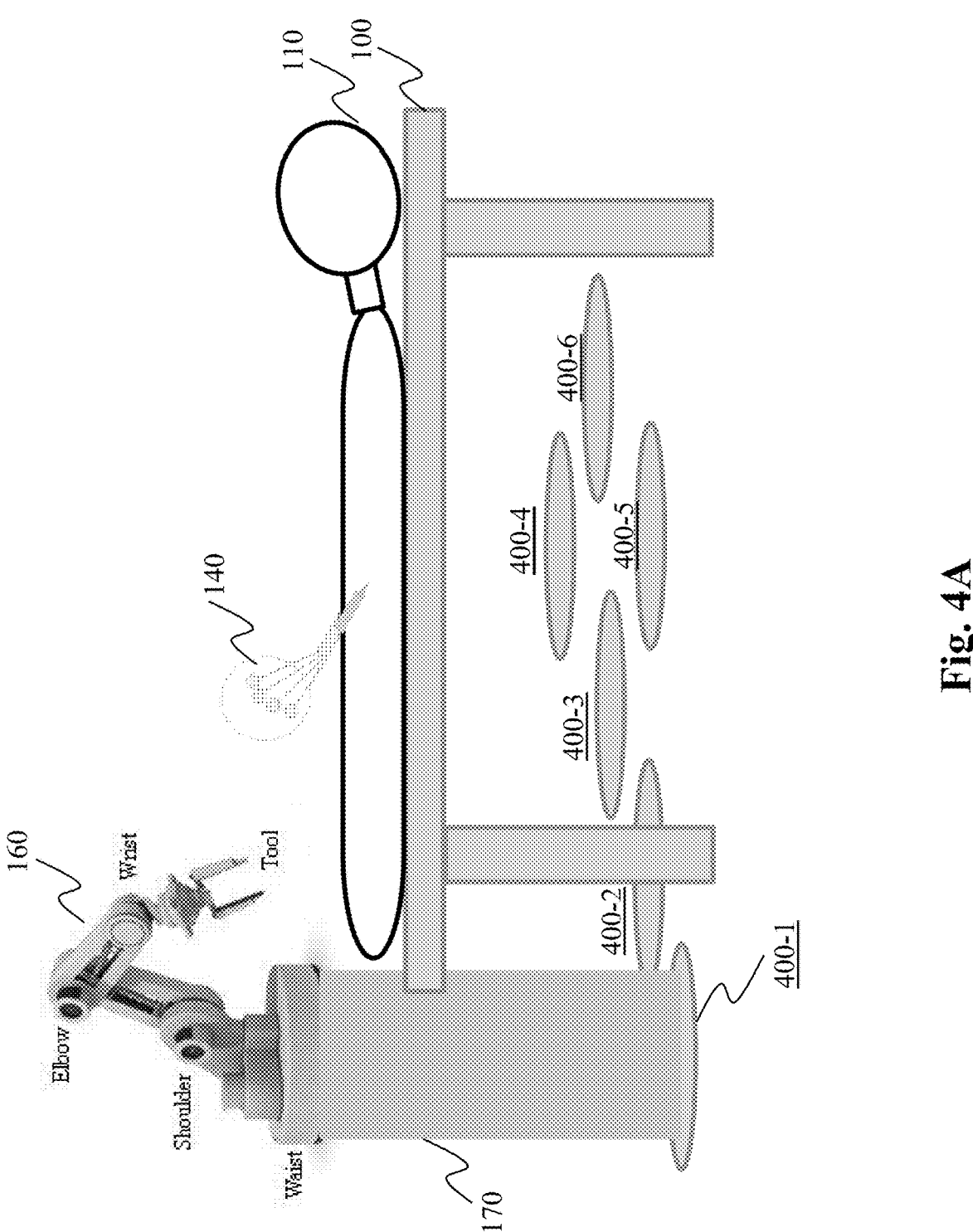
FIG. 4A depicts a surgical setting in which a robot may be placed at different base locations, in accordance with an embodiment of the present teaching.

With respect to surgical room configuration, the base location of a robot is also important in achieving efficient operation. Similar to trocar point locations, although robot 160 may be placed at any one of multiple base locations in a surgery room, some base locations lead to much better performance or efficiency than others. The present teaching discloses different embodiments in determining viable base locations according to different considerations and optimizations thereof in different situations. FIG. 4A depicts a surgical setting in which robot 160 may be placed at different base locations, in accordance with an embodiment of the present teaching. As seen, robot 160 with its base may be positions around a surgical bed at one of multiple locations, e.g., 400-1, 400-2, 400-3, 400-4, 400-5, . . . , and 400-6.

Figure 4B:
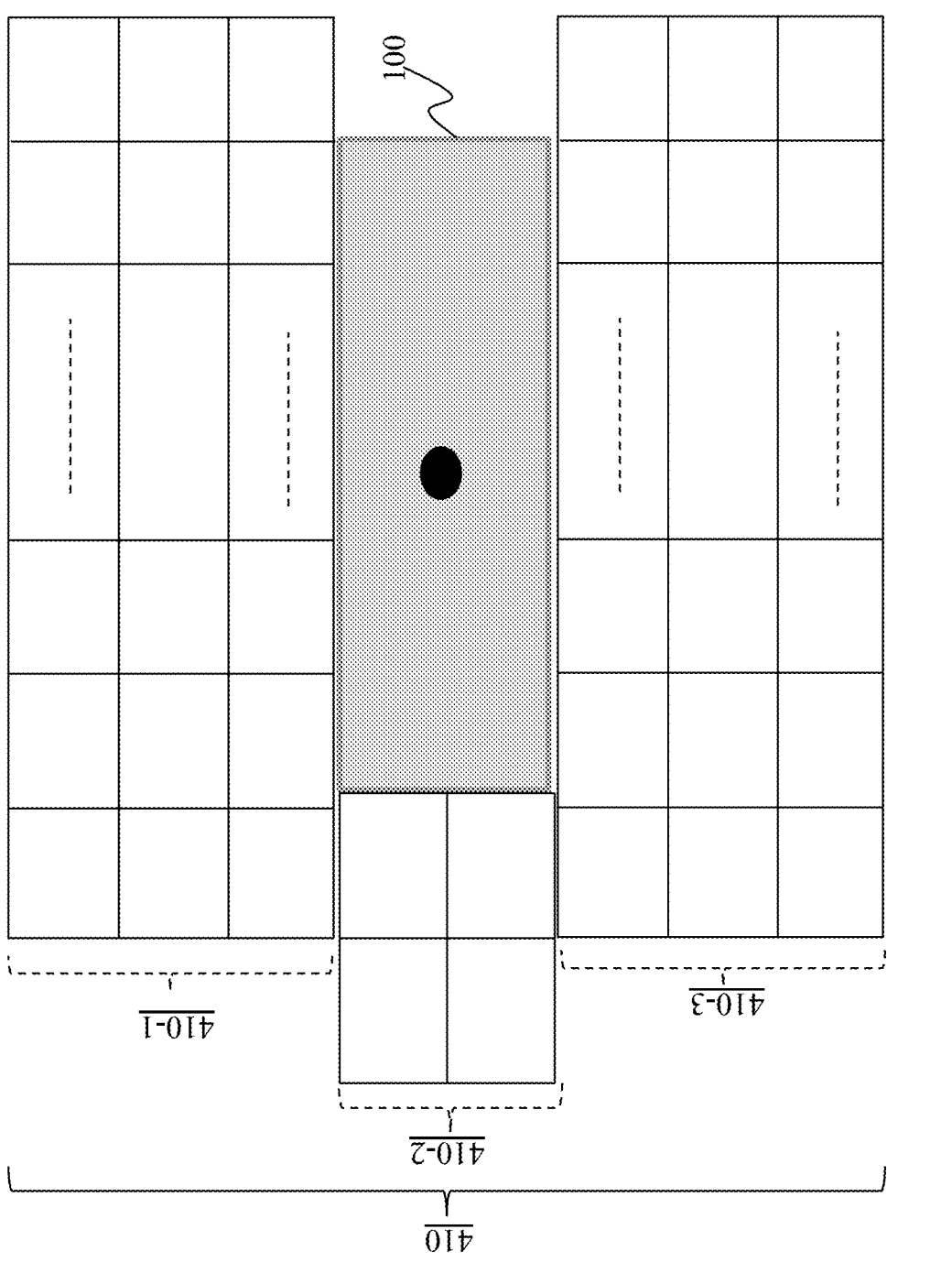
FIG. 4B is shows different robot base locations around a surgical table organized as an operating space grid, in accordance with an embodiment of the present teaching.

There may be more available base locations around the surgical bed, as shown in FIG. 4B, where the operating space around a surgical bed 100 may provide illustratively multiple viable base locations 410 on three sides. In this illustration, on each side of the surgical bed 100, the operating space may be divided into different regions, each of which may correspond to a candidate base location. As shown, along one side 410-1 of the surgical bed 100, available base locations form rows and columns of possible base locations like a grid. On the other side 410-3, there may also be rows and columns of subregions, each of which corresponds to an available base location. A third side 410-2 similarly depicts available base locations to deploy robot 160. Although base locations may be arranged as a grid with rows and columns in this example, other arrangements may also be possible. The way to determine available base locations may be determined based on application needs. For example, depending on whether other pieces of equipment may also need to be placed near a surgical bed, the available region for placing a robot may be limited and such candidate locations may not be adjacent to each other. Similar to trocar locations, base locations may also need to be evaluated based on certain criteria in order to maximize the performance and/or efficiency of robot 160 with respect to its intended functions.

Although robot 160 may be able to perform the intended functions at different base locations, different base locations may yield different performance or results. For instance, robot 160 may be used to move a surgical instrument inserted into a patient via a trocar point in such a way that the tip 130 reaches different cut points on a target organ. In this case, at some base locations, it may be more difficult than others for the robot to do the job. At some base locations, robot 160 to operate in a space too close to its singularity, which is undesirable. To evaluate different base locations, different criteria with respect to intended functions for the robot as well as the robot's own operating parameters may be considered.

Figure 4C:
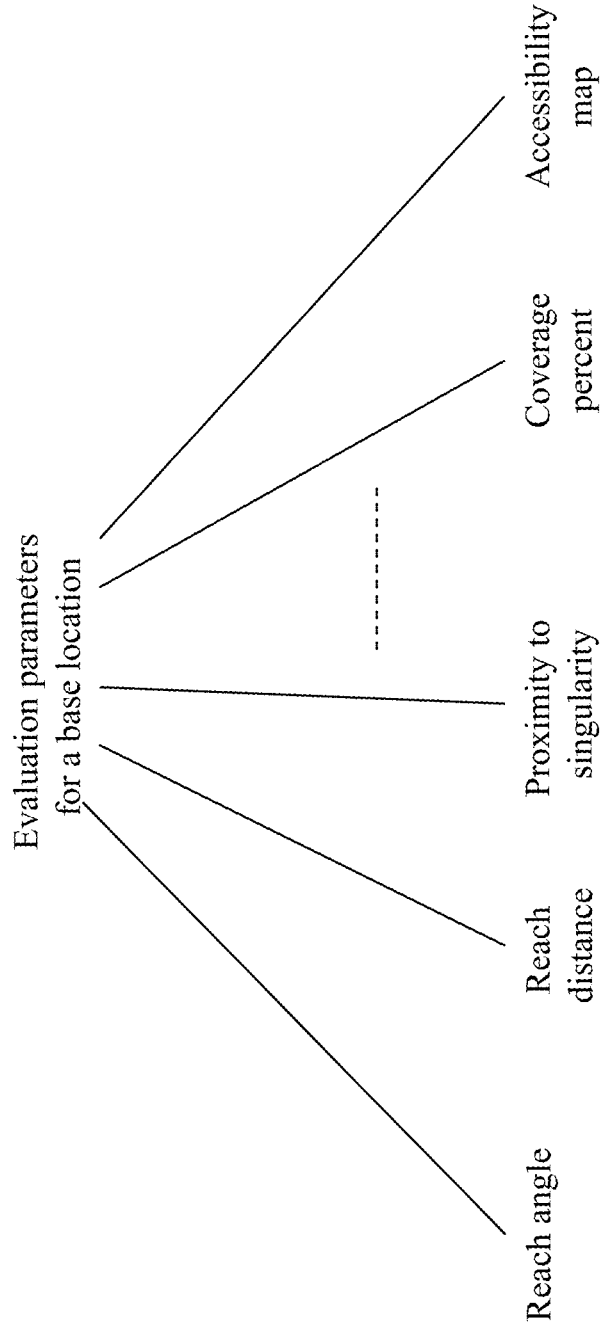
FIG. 4C shows different considerations in evaluating a robot base location, in accordance with an embodiment of the present teaching.

FIG. 4C presents different exemplary considerations in evaluating a robot base location, in accordance with an embodiment of the present teaching. In this illustration, the exemplary considerations may be provided according to the assumption that the robot is deployed to perform the function of controlling movement of a surgical instrument to operate on a target organ at certain cut points. Considerations in evaluating candidate robot base locations may include a variety of features. Some examples may include the kinematic feasibility of the robot arm with respect to the access map of the surgical tool, which may be based on to determine the access map of the robot, which may be generated by combining the robot base locations where there is a complete robot kinematic feasibility. Other features that may be considered in the evaluation may include the distance from the trocar to the robot base location, proximity of singularity, and a minimum distance between the robot and other robots, instruments, or obstacles. In some embodiments, other additional features may also be evaluated, including an angle between the arm and the surgical instrument with respect to a reference such as the surface norm at the trocar point and a percent of the cut points that can be reached by the surgical instrument based on the robot's access map. It is noted that these are exemplary features to be considered during evaluation are provided merely for illustration rather than limitation. Other criteria may also be applied, and they are all within the scope of the present teaching. For example, if the intended function of the robot is different, a different set of criteria with respect to the intended function may also be developed in order to assess appropriateness of different base locations.

Another aspect of the issue is the interplay between trocar point locations and robot's base locations. The appropriateness of a choice of one is not independent of the other. As such, an appropriate setting for a surgical environment needs to consider both. As discussed herein, there are different solutions to find an optimal combination of a trocar location and a base location, including sequential solutions or simultaneous solutions, each of which may be implemented via different embodiments. Below, exemplary solutions and embodiments are disclosed with reference to corresponding figures.

Figure 5A:
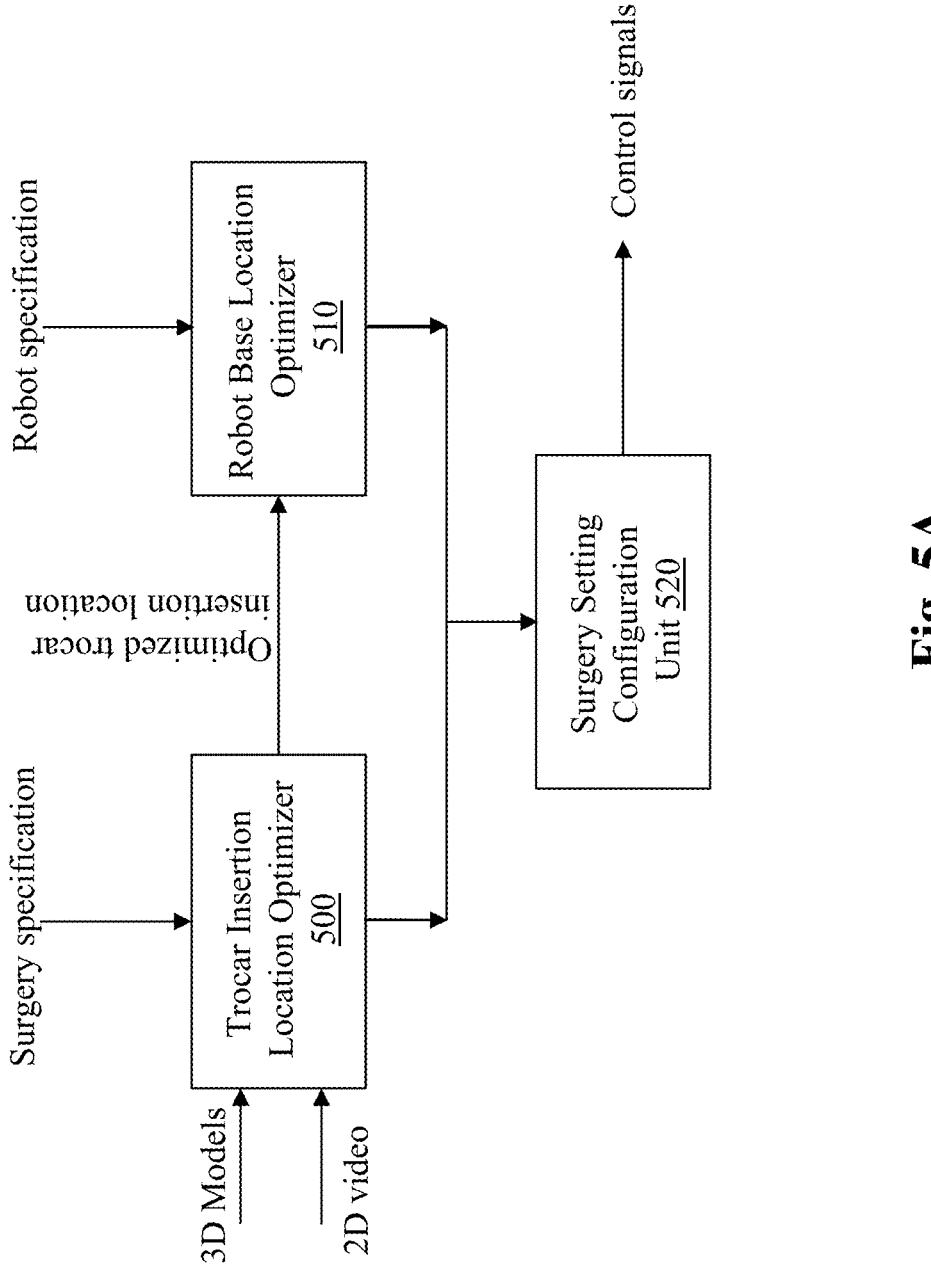
FIG. 5A depicts an exemplary high level system diagram of a sequential optimization scheme for determining trocar and robot base locations in a surgical setting, in accordance with an embodiment of the present teaching.

FIG. 5A depicts an exemplary high level system diagram of a sequential optimization framework 500 for determining trocar and robot base locations in a surgical setting, in accordance with an embodiment of the present teaching. In this optimization scheme, the optimal trocar location and the optimal base location for the robot are determined in a sequential order, i.e., first the trocar point location is optimized and then based on the optimized trocar point location, the base location for the robot is optimized. Accordingly, the illustrative sequential optimization framework 500 comprises a trocar insertion location optimizer 510, a robot base location optimizer 520, and a surgery setting configuration unit 530. The trocar insertion location optimizer 510 is for determining an optimal location on the skin of a patient as the trocar entry point and may be determined based on various considerations, some of which are illustrated in FIG. 3B. The robot base location optimizer 520 is for determining, given the optimal trocar location from the trocar insertion location optimizer 510, an optimal base location for the robot. As discussed herein, different considerations may also be applied to do so, some of which are illustrated in FIG. 4C. When both optimal trocar insertion location and base location are determined, they are used by the surgery setting configuration unit 530 to configure the surgery setting accordingly, which may include marking, in the 3D real life setting, e.g., the 3D coordinates of the optimal locations. For example, the marked 3D coordinate of the optimized trocar insertion location may provide guidance as to where a surgical instrument is to be inserted. If a user is to insert the surgical instrument, a marking on the patient's skin helps the user to see the location. If the robot is to be used to insert the surgical instrument, the surgery setting configuration unit 530 may determine a path for the robot arm to reach the surgical instrument as well as the kinematic parameters needed to control the robot to operate to achieve that. Such control signals may then output to the robot to execute the action.

Figure 5B:
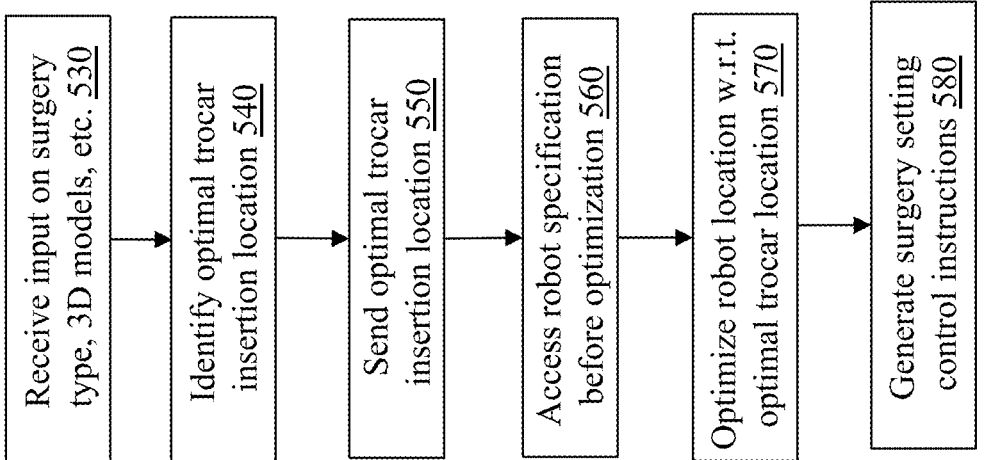
FIG. 5B is a flowchart of an exemplary process of a sequential optimization scheme for determining trocar and robot base locations in a surgical setting, in accordance with an embodiment of the present teaching.

FIG. 5B is a flowchart of an exemplary process of the sequential optimization framework 500 for determining trocar and robot base locations in a surgical setting, in accordance with an embodiment of the present teaching. Before the optimization takes place, various inputs are received at 540, including, e.g., the type of surgery (e.g., resection of a liver), 3D models of the organ involved (e.g., a 3D model for a liver with information about a resection trajectory), . . . , and specification about the robot to be used (e.g., type of robot, operation range, singularity, etc.). These inputs are important because the optimization is performed with respect to the limitations implicated by such inputs. With relevant inputs such as surgery type and 3D models with surgery path information, the trocar insertion location optimizer 510 identifies, at 550, an optimal trocar insertion location and sends it, at 560, to the robot base location optimizer 520. Upon receiving the optimized trocar insertion location, the robot base location optimizer 520 proceeds to identify, at 570, an optimized base location with respect to the optimized trocar location. Both optimized trocar insertion location and robot base location are then sent, at 580, to the surgery setting configuration unit 530 in order to generate, at 590, various control signals to be used to place the surgical instrument at the optimized trocar point and the robot at the optimized base location.

Figure 6A:
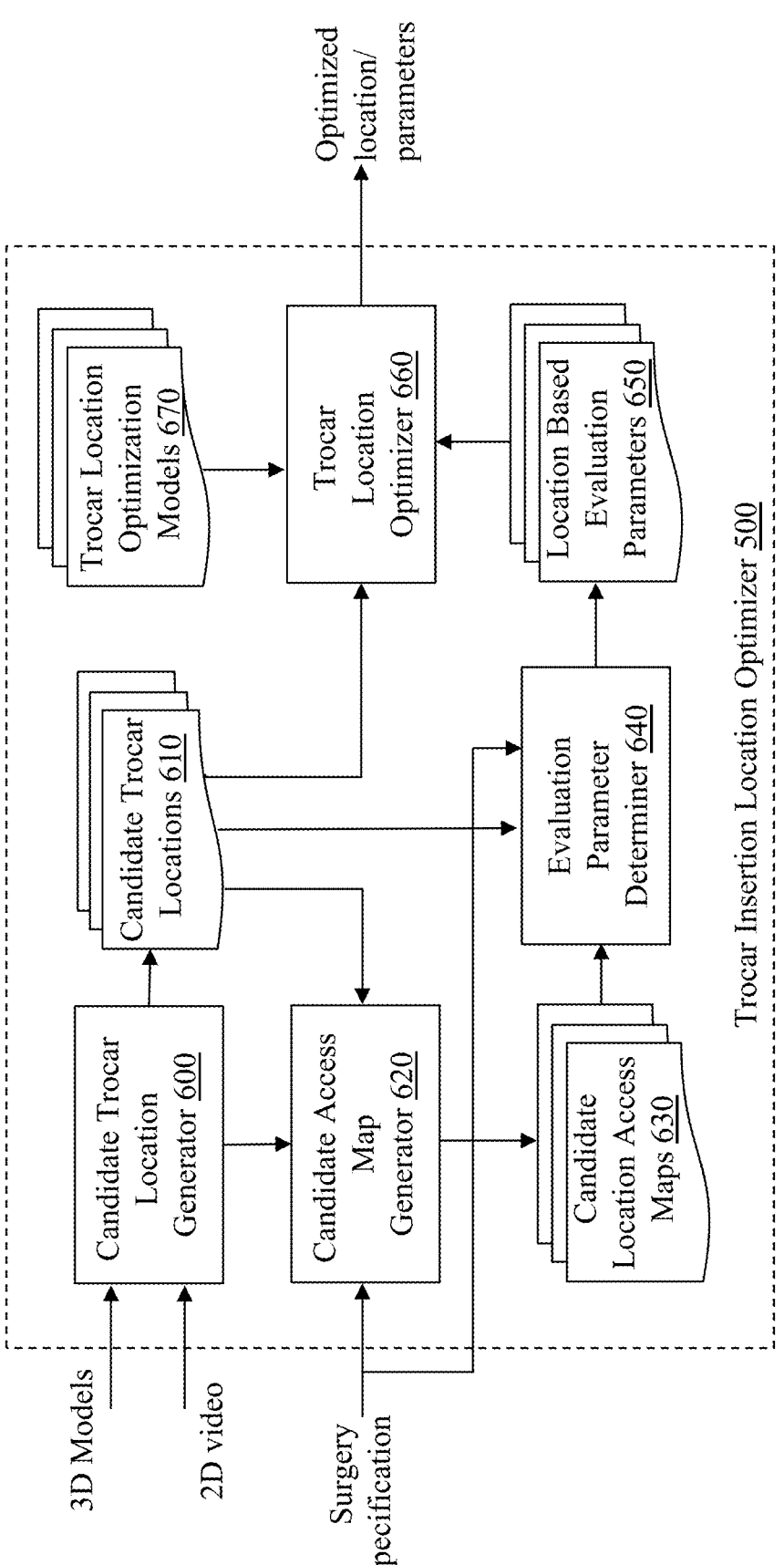
FIG. 6A is an exemplary high level system diagram of a trocar insertion location optimizer, in accordance with an embodiment of the present teaching.
Figure 6B:
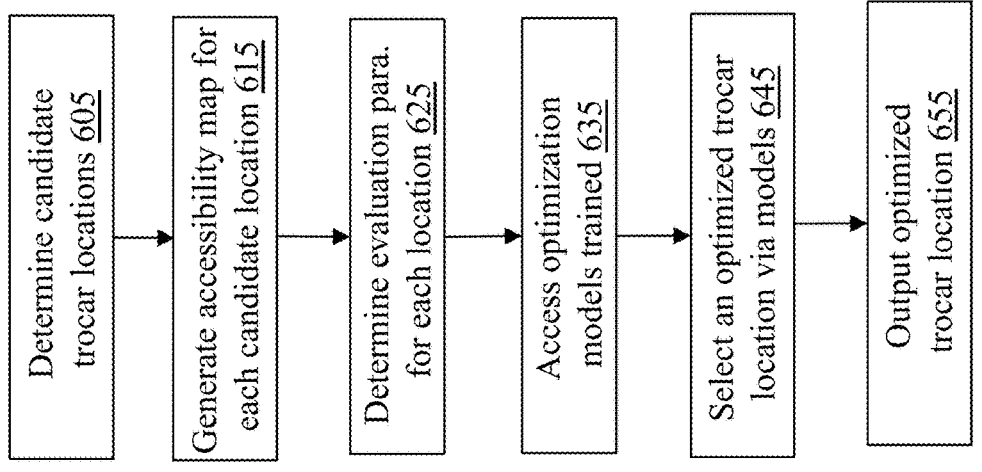
FIG. 6B is a flowchart of an exemplary process of a trocar insertion location optimizer, in accordance with an embodiment of the present teaching.

FIG. 6A is an exemplary high level system diagram of the trocar insertion location optimizer 510, in accordance with an embodiment of the present teaching. In this illustrated embodiment, the trocar insertion location optimizer 510 comprises a candidate trocar location identifier 600, a candidate access map generator 620, an evaluation feature determiner 640, and a trocar location optimizer 660. FIG. 6B is a flowchart of an exemplary process of the trocar insertion location optimizer 510, in accordance with an embodiment of the present teaching. In operation, candidate trocar locations may be determined, at 605, by the candidate trocar location identifier 600. There may be different ways to determine such candidate locations. For instance, with input of the 3D models for an organ with information about a surgery trajectory incorporated therein, a candidate trocar location may be determined based on, e.g., along an average surface norm of the cut points on the surgery trajectory or along each of the surface norms of some cut points selected according to some interval along the surgery trajectory. The selection of cut points may be accomplished by a user based on visual information in 2D video displaying the organ as captured by a sensor inside of the patient. The identified candidate trocar insertion locations are then saved in 610 and are used to determine, at 615 by the candidate access map generator 620, an access map for each of the candidate trocar insertion location. The access maps so generated for the candidate trocar insertion locations are then saved in 630.

To facilitate optimization, for each of the candidate trocar insertion locations, various evaluation features may be determined, at 625, for assessment as illustrated in FIG. 3B. For example, the kinematic reachability of the robot to the access map of the surgical tool, the coverage of the cut points on the surgery trajectory (specified by the 3D model) by the access map of each candidate trocar insertion location, the average angle and distance from the trocar point to the cut points, etc. may be determined by the evaluation feature determiner 640 and saved as location based evaluation parameters 650. Based on such evaluation parameters for each of the candidate trocar insertion locations, the trocar location optimizer 660 may then access, at 635, optimization models 670 and accordingly select, at 645, an optimized trocar insertion location based on the optimization models 670. In some embodiments, the optimization models may be obtained via machine learning based on historic surgery setting information versus the surgery performance. Such optimized trocar insertion location may then be output at 655 as the optimization result.

Figure 7A:
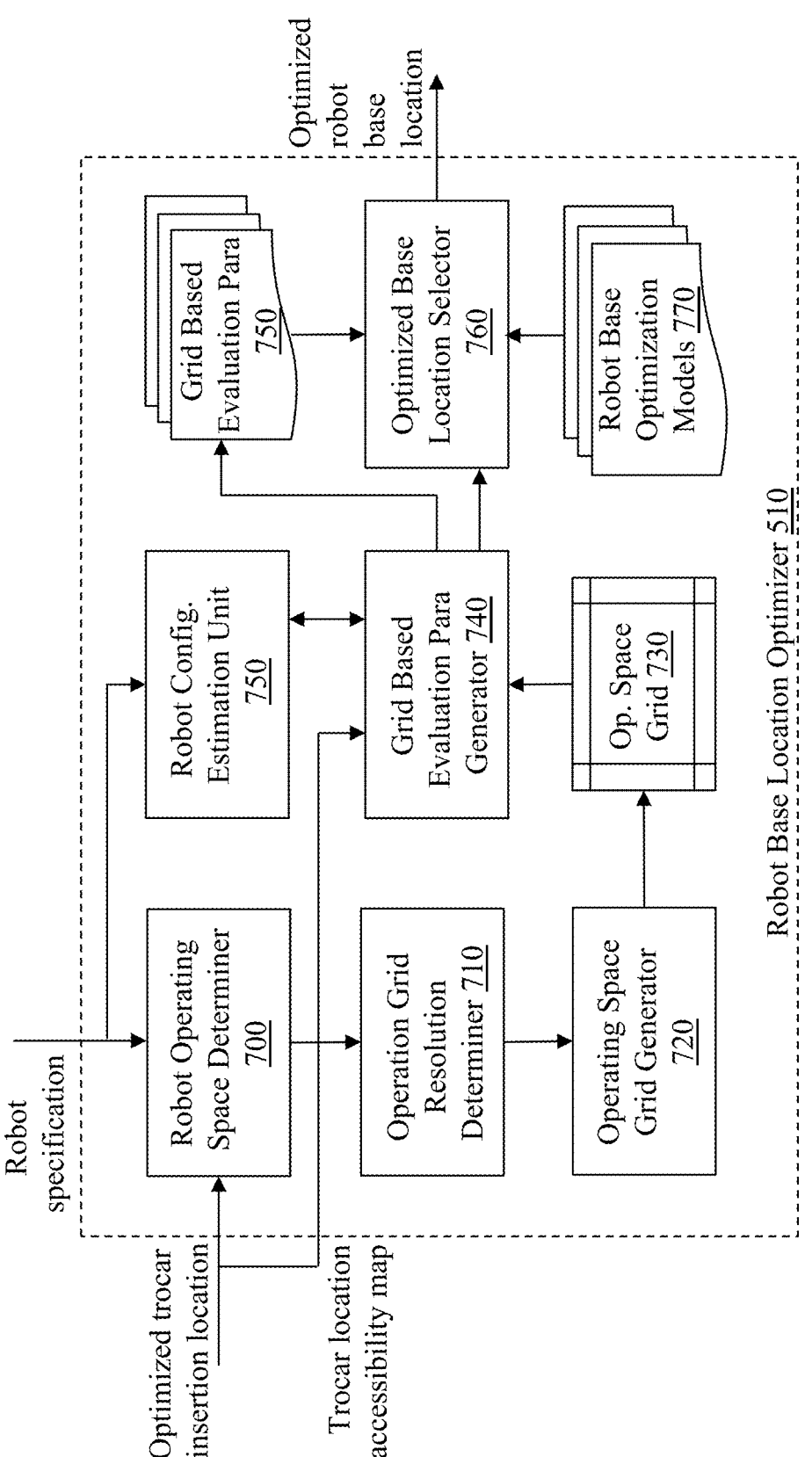
FIG. 7A depicts an exemplary high level system diagram of a robot base location optimizer, in accordance with an embodiment of the present teaching.

FIG. 7A depicts an exemplary high level system diagram of the robot base location optimizer 520, in accordance with an embodiment of the present teaching. In this illustration, the robot base location optimizer 520 comprises a robot operating space determiner 700, a grid resolution determiner 710, an operating space grid generator 720, a grid based evaluation parameter generator 740, a robot configuration unit 750, and an optimal base location selector 760. As discussed herein, in a sequential optimization scheme, the optimization of robot base location is performed with respect to an optimized trocar insertion location. As such, the candidate base locations of the robot may be determined with respect to the input optimized trocar insertion location and the evaluation of each grid base location may be based on the access map of the optimized trocar insertion location.

In operation, the robot base location optimizer 520 may first identify an operating space in which the robot is capable of performing its intended function given the optimized trocar insertion point. The operating space includes multiple viable base locations as candidate base locations. To optimize, each of the candidate locations may be individually evaluated and such evaluation results may then be used to identify a best one. To obtain candidate base locations, the operating space of the robot is divided into grids according to a resolution specified as an optimization parameter. Each of the grids corresponds to a candidate base location. Then each grid in the operating space is evaluated in terms of operation of the robot with respect to the optimized trocar insertion location and the intended function to be performed by the robot. For example, the robot at a base location may be evaluated in terms of whether it can cover the access map of the optimal trocar insertion point. Some of the evaluation criteria for a robot base location are illustrated in FIG. 4C. An optimized base location is selected based on the evaluation results.

Figure 7B:
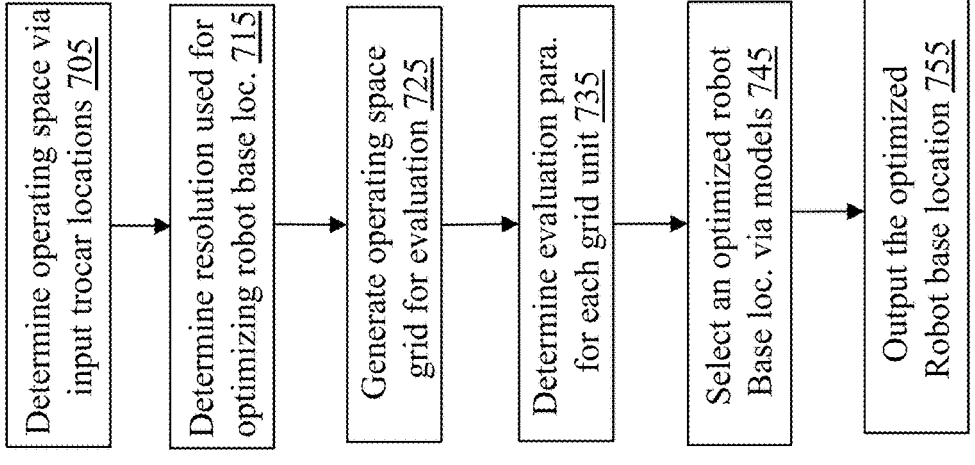
FIG. 7B is a flowchart of an exemplary process of a robot base location optimizer, in accordance with an embodiment of the present teaching.

FIG. 7B is a flowchart of an exemplary process of the robot base location optimizer 520, in accordance with an embodiment of the present teaching. In operation, when the optimized trocar insertion location with an access map is received, the robot operating space determiner 700 determines, at 705, an operating space for the robot with respect to the optimized trocar insertion location (the operable space for the robot is related to the trocar insertion location). To optimize, the evaluation is performed with respect to each possible candidate base location. In this illustrated embodiment, the operating space is divided into grids, each of which corresponds to a candidate base location. To do so, the grid resolution determiner 710 first determines, at 715, the resolution to be used to divide the operating space into different grids. For example, the grid resolution may be set based on the dimension of the base of the robot.

Based on the grid resolution, the operating space grid generator 720 creates, at 725, an operating space grid 730 with candidate base locations corresponding to the individual grids. Based on the operating space grid 730, the grid based evaluation parameters generator 740 determines, at 735, evaluation parameters for each of the candidate base locations in the operating space grid based on inputs such as the optimized trocar insertion location and its access map and the configurations of the robot needed to achieve what is intended. The results of the evaluation of each of the candidate base locations are saved in 750 and are used by the optimal base location selector 760 to select, at 745, an optimal base location. The selection may be performed in accordance with robot base optimization models 770. In some embodiments, the robot base optimization models 770 may provide, e.g., specified discrete optimal ranges of different evaluation criteria. In some embodiments, the robot base optimization models 770 may correspond to machine learned models that are trained based on, e.g., historic data collected from different surgeries with setting configuration information, performance rating of the surgeries, operation incident evaluation data, etc. With machine learned robot base optimization models 770, the grid based evaluation parameters for all candidate base locations may be input to the models and the output may correspond to a selected base location as the optimal choice. The optimal base location is then output, at 755, as the optimization result for robot base location.

Figure 7C:
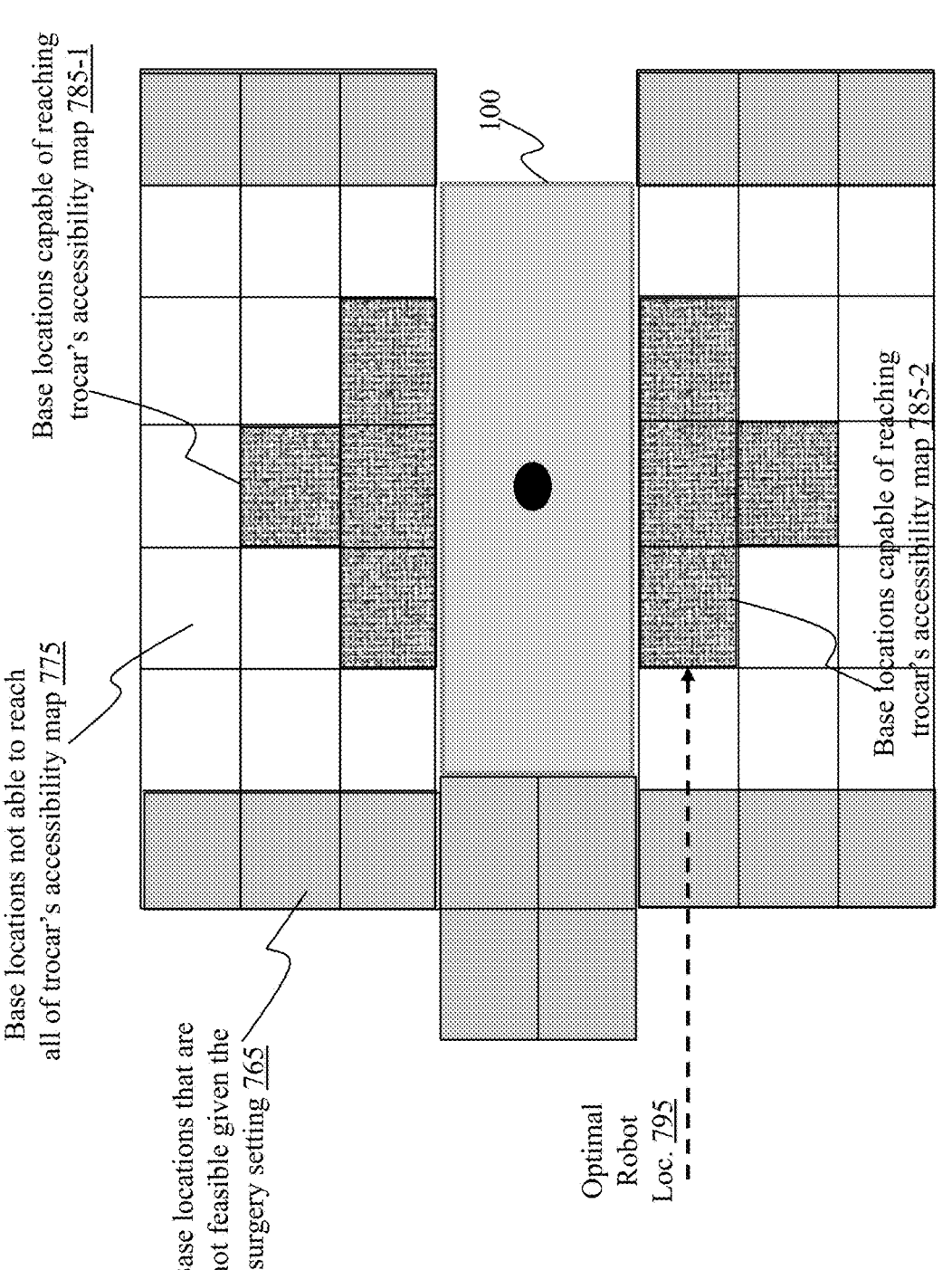
FIG. 7C illustrates exemplary classification of robot base locations organized as an operating space grid, in accordance with an embodiment of the present teaching.

FIG. 7C illustrates exemplary classification of robot base locations in an operating space grid, in accordance with an embodiment of the present teaching. In this example, the operating space grid includes multiple ones on three sides of a surgical bed 100. Each base location in the grid is classified and represented using different types of texture. For example, there are base locations in the grid with gray (765) classified as base locations that are not feasible given the surgery setting. For instance, from those base locations marked gray, it may be impossible for the robot to reach, e.g., the surgical instrument. In addition, there are also base locations in the grid without texture marking (775) classified as ones from where the robot is not able to cover all area of the trocar point's access map. Furthermore, there are base locations in the grid that are marked with texture (785 including, e.g., base locations 785-1 and 785-2 on both sides of the surgical bed) to represent base locations from where the robot is capable of covering the entire access map associated with the trocar insertion point. That is, each of the base locations in 785 is qualified as a candidate base location. As discussed herein, such candidate robot base locations may be combined to form the access map (785) of the robot. Through optimization, one of the base locations in the class 785 may be selected as an optimal base location 795 based on the evaluation results.

Figure 8A:
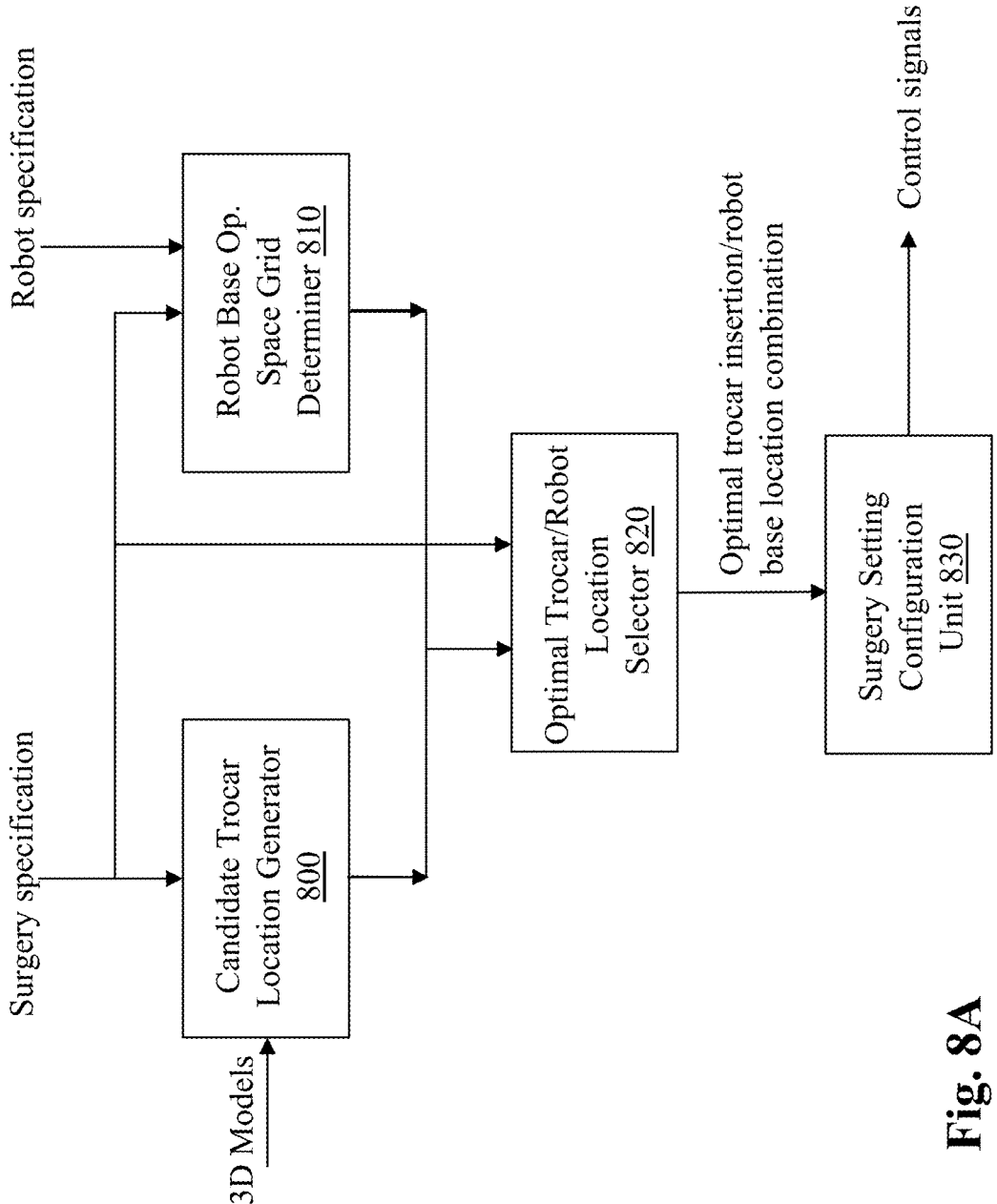
FIG. 8A depicts an exemplary high level system diagram of a simultaneous optimization scheme for determining optimal trocar and robot base locations in a surgical setting, in accordance with an embodiment of the present teaching.

As discussed herein, another mode of optimization according to the present teaching is simultaneously optimizing a combination of a trocar insertion and robot base locations. FIG. 8A depicts an exemplary high level system diagram of a simultaneous optimization framework 800 for determining optimal trocar and robot base locations in a surgical setting, in accordance with an embodiment of the present teaching. In this embodiment, the simultaneous optimization framework 800 includes a candidate trocar location generator 810, a robot operating space grid generator 820, an optimal trocar/robot combination selector 830, and a surgery setting configuration unit 840. In this framework, both candidate trocar location generator 810 and robot operating space grid generator 820 are used to determine candidate locations for both trocar insertion and robot without selection. All candidates of trocar and robot locations are sent to the optimal trocar/robot combination selector 830 where combinations of trocar and robot locations are considered, and an optimal combination is selected as optimized combination. The optimized combined trocar insertion location and the robot location are then sent to the surgery setting configuration unit 840, which performs the same function as what is described for 530.

Figure 8B:
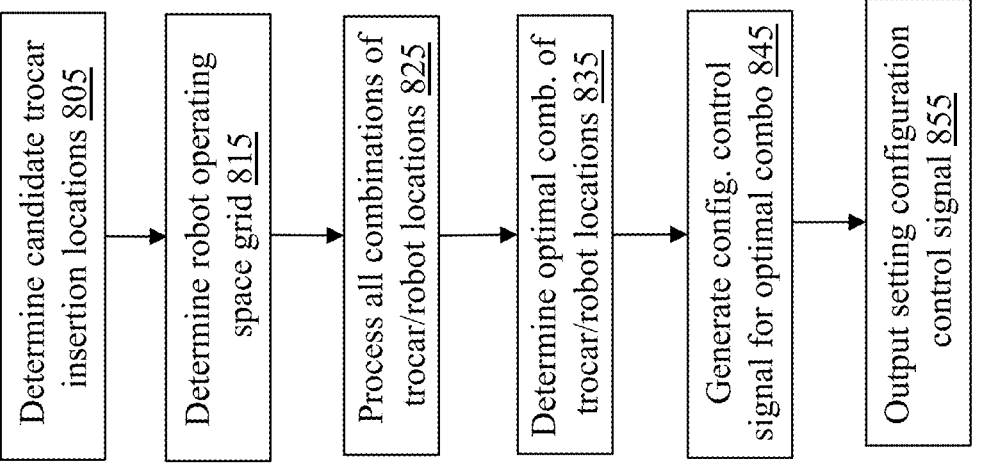
FIG. 8B is a flowchart of an exemplary process of a simultaneous optimization scheme for determining optimal trocar and robot base locations in a surgical setting, in accordance with an embodiment of the present teaching.

FIG. 8B is a flowchart of an exemplary process of the simultaneous optimization scheme 800 for determining optimal trocar and robot base locations in a surgical setting, in accordance with an embodiment of the present teaching. Based on input information, the candidate trocar location generator 810 determines, at 805, candidate trocar insertion locations and send such candidates to optimal trocar/robot combination selector 830. Similarly, robot operating space grid generator 820 determines, at 815, the robot operating space grid, where each grid represents a candidate robot base location. The generated robot space operating space grid is sent to optimal trocar/robot location selector 830 as candidate base locations. Upon receiving the candidate trocar insertion locations as well as candidate base locations for robot, the optimal trocar/robot combination selector 830 processes all combinations of trocar/base locations at 825 and determines, at 835, the optimal combination for trocar insertion and the robot base location. Such selected optimal combination is then sent to the surgery setting configuration unit 840, which generates, at 845, configuration control signals based on the received optimal trocar insertion location and the robot base location. The control signals are then output at 855 so that the surgery room may be configured according to the optimization results.

Figure 9A:
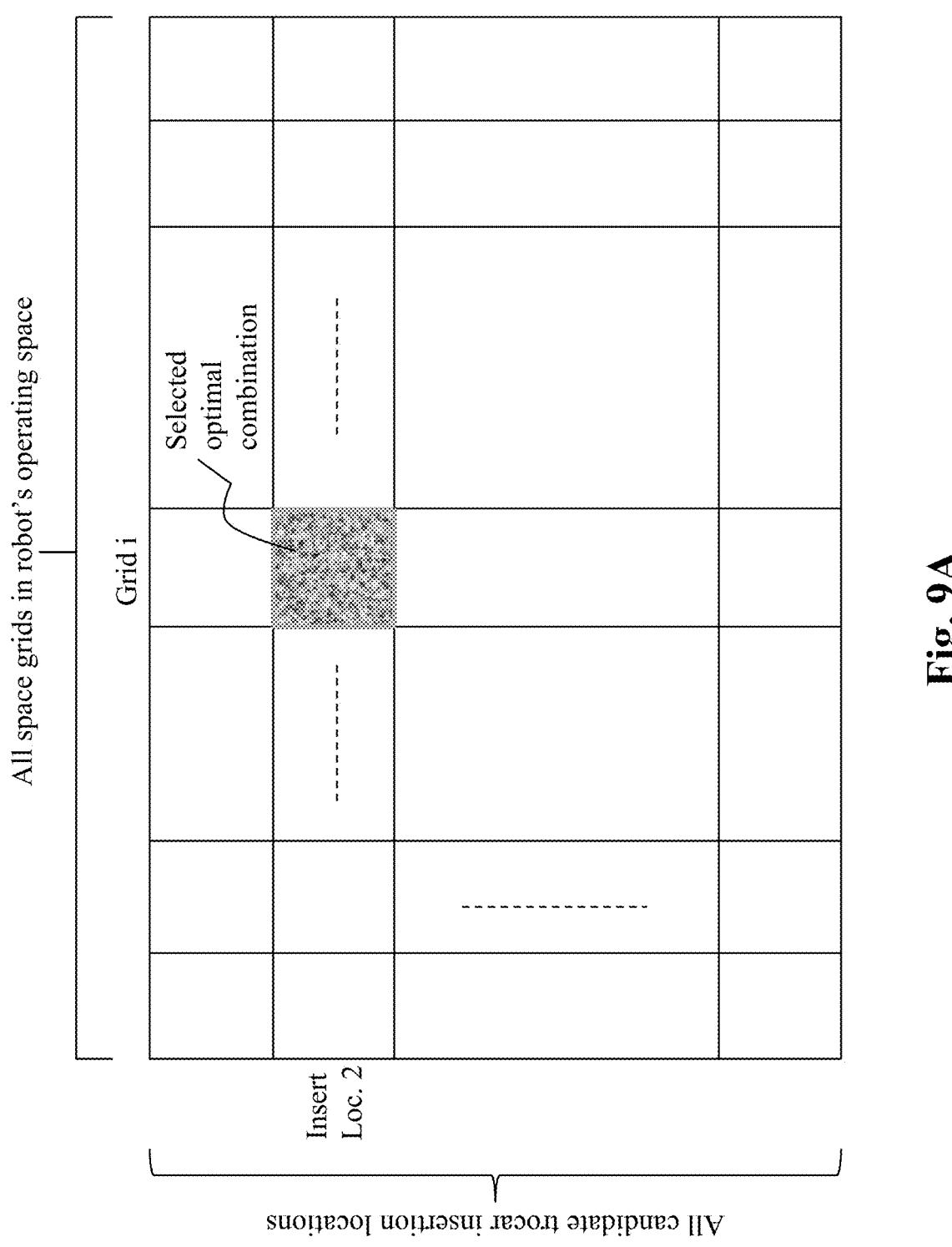
FIG. 9A illustrates an exemplary matrix of all combinations of possible trocar and base locations for simultaneous optimization, in accordance with an embodiment of the present teaching.

In optimizing combinations of trocar and robot base locations, each combination is to be evaluated. If there are M candidate trocar insertion locations and N robot base locations, the number of combinations to be considered is MxN. This is illustrated in FIG. 9A, which illustrates an exemplary combination matrix 900 for simultaneous optimization of a trocar and robot base location combination, in accordance with an embodiment of the present teaching. In this exemplary matrix, each row corresponds to one candidate trocar insertion location and each column represents one candidate robot base location. The optimization is to select one cell, as 910 shown in FIG. 9A, representing a particular combination of a trocar insertion and robot base locations.

Figures 9B, 9C:
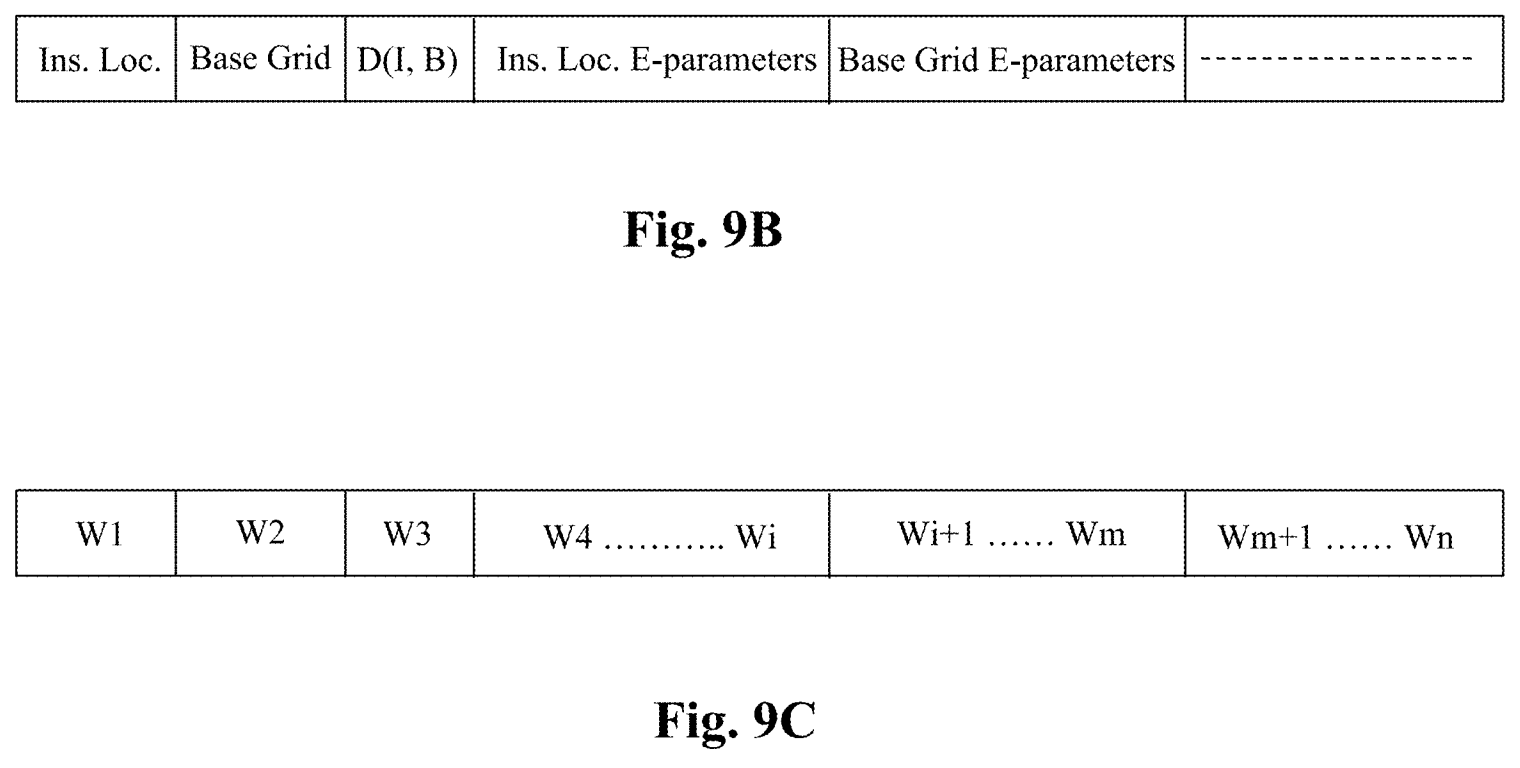

To be able to select one combination as illustrated in FIG. 9A, every combination in the combination matrix 900 has to be evaluated. As discussed herein, there may be various criteria to be applied with respect to each trocar insertion location and/or robot base location, as illustrated in FIGS. 3B and 4C. When considering trocar and robot base locations in combination, additional considerations may be added such as the spatial relationship between the two, including a distance between the two and an angle formed by the two locations, etc. The features that are included in evaluating a combination may be organized as a feature vector as illustrated in FIG. 9B, where an exemplary feature vector 920 is shown to represent a pair of trocar and robot base locations, in accordance with an embodiment of the present teaching. In this example, feature vector 920 in FIG. 9B may include many features related to a candidate trocar insertion location, a candidate base location information, and features indicative of their spatial relationships. For example, feature 920-1 may be the location of the candidate trocar point, feature 920-2 may be the candidate base location, feature 920-3 or D(I,B), may represent the distance between the two locations, feature 920-4, or A(I,B), may correspond to an angle formed by the two with respect to some reference, . . . , insertion location evaluation parameters 920-i, . . . , and base location evaluation parameters 920-k, . . . . That is, each cell in the combination matrix 900, representing a combination, is associated with a feature vector that is to be used by the optimal trocar/base combination selector 830 for evaluation.

The optimal trocar/base combination selector 830 may be realized in different ways to select the optimal combination. In some embodiments, a weighted sum based on approach may be adopted, which may evaluate different combinations based on their weighted feature vector values. FIG. 9C illustrates an exemplary weight vector 930 with weights therein corresponding to respective features in a feature vector for a combination, in accordance with an embodiment of the present teaching. The exemplary weights in the vector include W1, W2, . . . Wi, . . . , Wm, . . . , Wn, each of which is used to weigh a feature value in the feature vector 920 to obtain a weighted sum for each feature vector. Then the selection of an optimal combination may be based on the weighted sum values. In some embodiments, the weights Wi, 1<i<=n, may be trained via machine learning based on, e.g., historic data collected from different surgeries, as discussed herein.

Figure 10A:
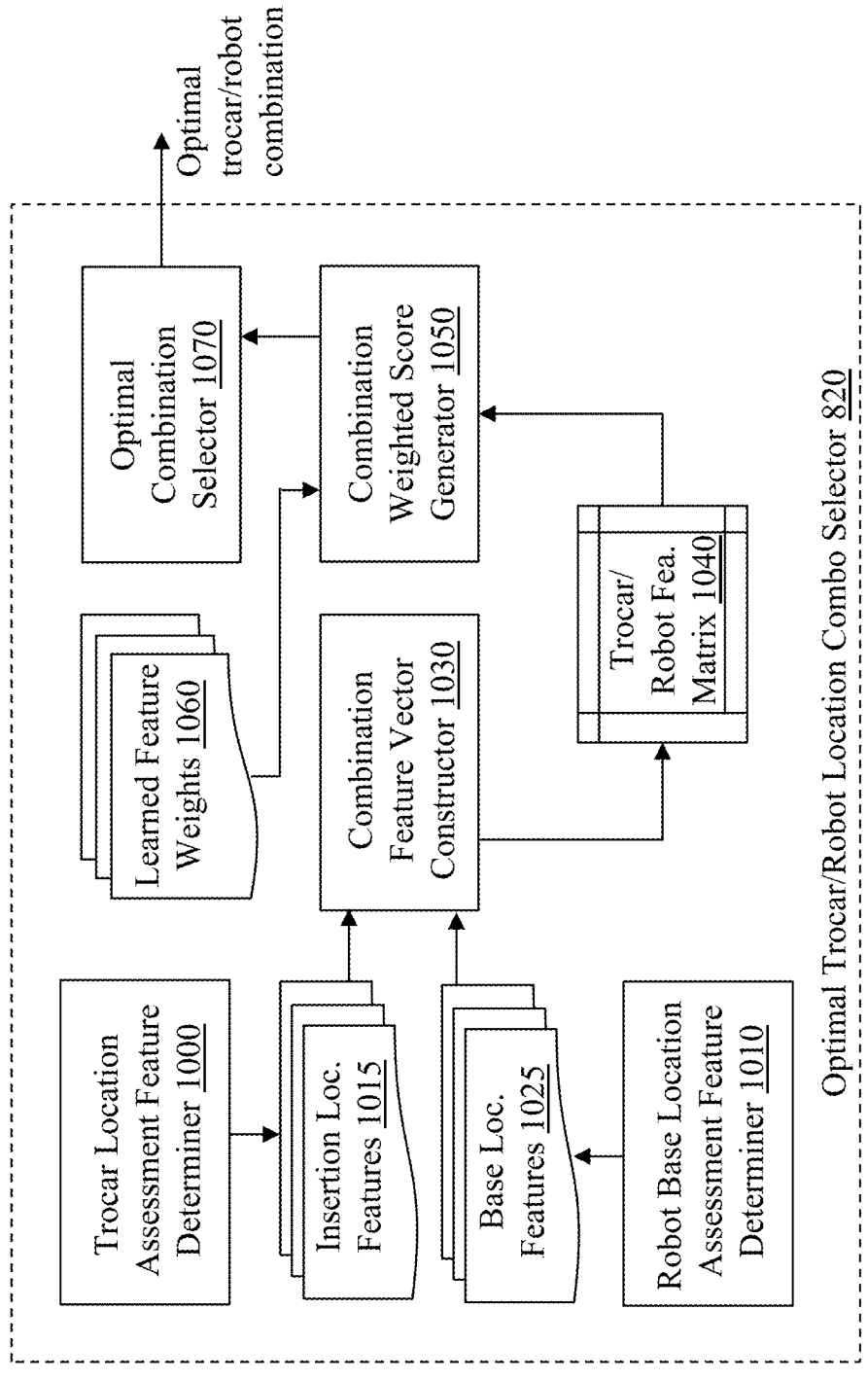
FIG. 10A depicts an exemplary high level system diagram of an optimal trocar/robot combination selector, in accordance with an embodiment of the present teaching.
Figure 10B:
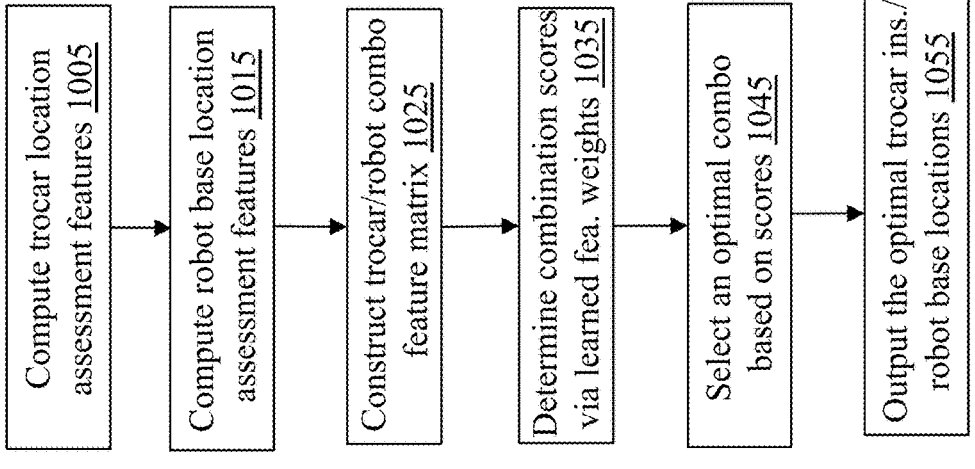
FIG. 10B is a flowchart of an exemplary process of an optimal trocar/robot combination selector, in accordance with an embodiment of the present teaching.

FIG. 10A depicts an exemplary high level system diagram of the optimal trocar/robot location combination selector 830 based on the weighted sum solution, in accordance with an embodiment of the present teaching. In this illustrated implementation, the optimal trocar/robot combination selector 830 includes a trocar location assessment feature determiner 1000, a robot base location assessment feature determiner 1010, a combination feature vector constructor 1030, a combination weighted sum score generator 1050, and an optimal combination selector 1070. FIG. 10B is a flowchart of an exemplary process of the optimal trocar/robot combination selector 830, in accordance with an embodiment of the present teaching. In operation, when the combination matrix 900 is received as input with all combinations, for each combination of trocar/base locations (corresponding to a cell in matrix 900 in FIG. 9A), a feature vector for the combination needs to be constructed. To do so, some of the evaluation features associated with each location may need to be determined before they are incorporated into the combined feature vector. For example, the insertion location evaluation parameters 920-i (FIG. 9B) associated with the trocar point may be determined, at 1005, by the trocar location assessment feature determiner 1000 and saved in 1012. Similarly, the base location evaluation parameters 920-k (FIG. 9B) associated with the robot base location may be determined, at 1015, by the robot base location assessment feature determiner 1010 and saved in 1022. The assessment parameters for all trocar locations in all combinations are stored in 1012. The assessment parameters for all robot base locations in all combinations are stored in 1022.

Based on the computed assessment parameters in 1012 and 1022, the combination feature vector constructor 1030 computes, for each combination in the combination matrix 900 (input), a feature vector that includes the assessment parameters for both the trocar location and robot base location in the combination as well as other features. That is, for each of the cell in the combination matrix 900, there is a feature vector so that the combination feature vector constructor 1030 constructs, at 1025, a trocar/robot combination feature matrix 1040 for all combinations. Then the combination weighted sum score generator 1050 determines, at 1035, a weighted sum score for each of the combinations based on learned weights for different features stored in 1060. Based on the weighted sums for the combinations, the optimal combination selector 1070 selects, at 1045, an optimal combination according to the scores and outputs, at 1055, the selected optimal combination.

Other implementations may also be possible for selecting an optimal combination. For instance, the feature vectors may be ranked according to some specified criteria. In some embodiments, the ranking may be achieved by ranking the feature vectors based on some sorting criteria, which may indicate an order of some of the features in the feature vector. For instance, the sorting criteria may instruct to sort the feature vectors by using an ascending order of the distance between a trocar location and a base location, an ascending order of the angle between the two, . . . , a descending order of features related to evaluation scores, . . . , etc. The goal may be that through such sorting, the feature vectors are ranked according to desirability of the features so that an optimal combination may be selected from some top ranked feature vectors. In some embodiments, the top ranked combination may be selected. In other embodiments, an optimal combination may be selected from top ranked combinations according to some other additional considerations.

Figure 11A:
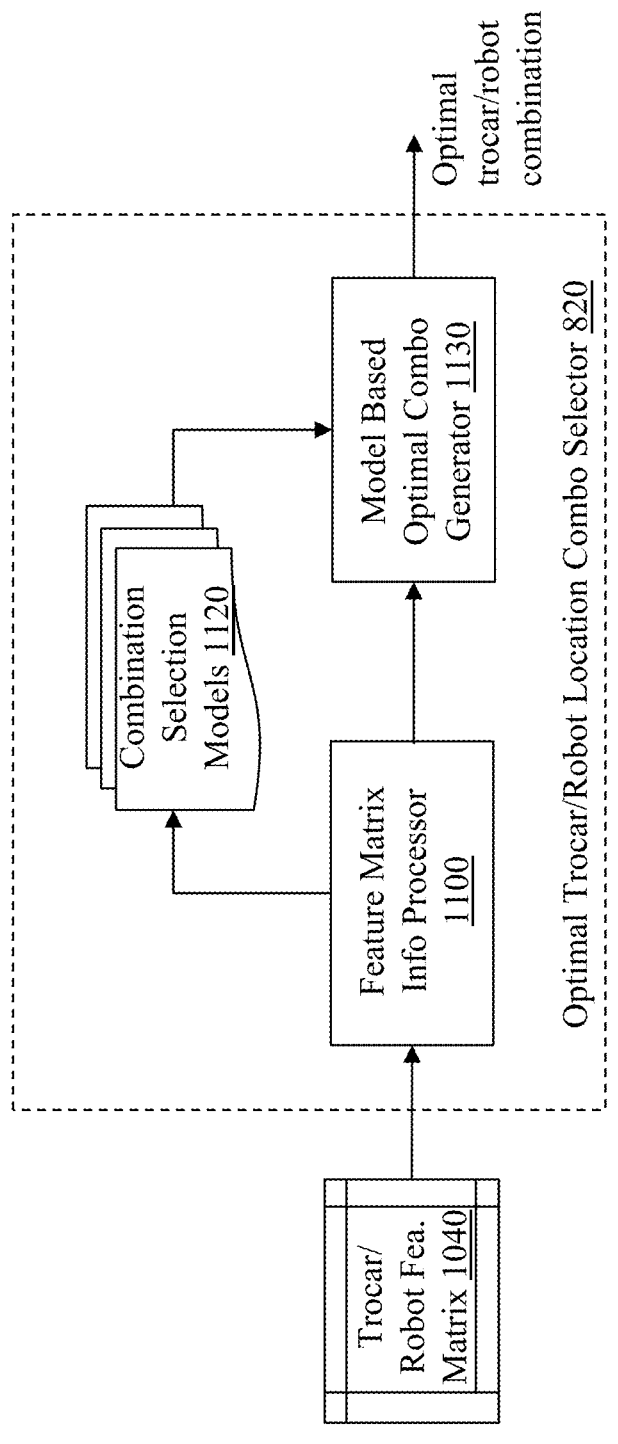
FIG. 11A depicts another exemplary high level system diagram of an optimal trocar/robot combination selector, in accordance with an embodiment of the present teaching.

As discussed herein, a different operational model for simultaneously optimizing the trocar insertion and robot base locations is via a model-based approach. FIG. 11A depicts an exemplary high level system diagram of a different realization of the optimal trocar/robot combination selector 830, in accordance with a different embodiment of the present teaching. In this mode of operation, the feature vectors for all candidate combinations in the combination matrix 900 are considered at the same time by machine trained models to identify optimal combination. In this embodiment, the optimal trocar/robot combination selector 830 comprises a feature matrix information processor 1100 and a model based optimal combination generator 1130.

Figure 11B:
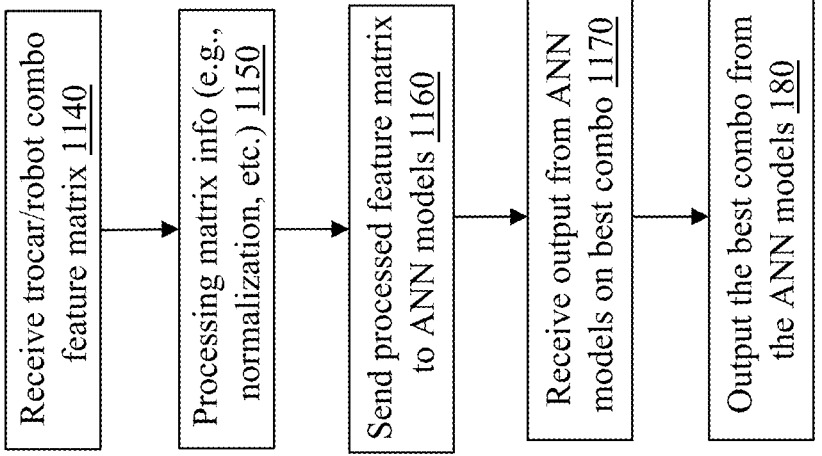
FIG. 11B is a flowchart of an exemplary process of another implementation for an optimal trocar/robot combination selector, in accordance with an embodiment of the present teaching.

FIG. 11B is a flowchart of an exemplary process of the optimal trocar/robot combination selector 830, in accordance with a different embodiment of the present teaching. In operation, the feature matrix information processor 1100 receives, at 1140, feature vectors in the trocar/robot base feature matrix 1040 as input and processes, at 1150, these input feature vectors to generated processed feature vectors. The processing that may be applied to the feature vectors may include, e.g., converting non-numeric feature values into numeric values, transform feature values to a certain ranges, or normalization of feature values, etc. The processed feature vectors may then be sent, at 1160, to machine trained combination selection models 1120 so that the processed feature vectors may be considered simultaneously by the models. The combination selection models 1120 may then produce an output, at 1170, corresponding to an optimal combination selected from the input processed feature vectors.

In some situations when the number of combinations is too high and the combination selector models 1120 may have a limitation on the number of input feature vectors which is smaller than the actual number of combinations, the feature matrix information processor 1100 and the model-based optimal combination generator 1130 may collaborate to operate in a batch processing mode. In the batch mode, the feature matrix information processor 1100 sends a batch of feature vectors each time to the models 1120. The feature matrix information processor 1100 may inform the model-based optimal combination generator 1130 the total number of feature vectors and the size of each batch. If the former is larger than the latter, the model-based optimal combination generator 1130 computes the batches needed to arrive the final optimal combination selection. When an optimal combination selected from a batch is received, the model-based optimal combination generator 1130 determines whether the received selection corresponds to a final optimal combination selected. If not, the received sub-optimal combination may be saved until all sub-optimal combinations are received. Then the sub-optimal combinations are used to inform the feature matrix information processor 1100 to generate a new final batch including the feature vectors corresponding to the selected sub-optimal combinations so that a final optimal combination may be selected by the combination selection models 1120. When the final optimal combination selection is received by the model-based optimal combination generator 1130, it outputs, at 1180, the optimal combination selected.

Different aspects of the present teaching have been disclosed. In different embodiments, models trained via machine learning may be used in performing different tasks, including trocar location optimization models 670 and robot base optimization models 770 used in the sequential optimization operation mode, as well as models for learned weights 1060 and combination selection models 1120 in simultaneous optimization operation mode. As discussed herein, these models may be trained via machine learning based on training data generated based on historic surgery setting information and the evaluations thereof. The historic data may be collected based on recorded surgery settings and some may be automatically collected, and some may be collected manually. The recordings of surgical room settings may be combined with recorded information related to ratings by doctors and nurses who participated in the surgeries.

Evaluations of each surgery setting may also be collected to guide the learning system to learn what is good and what is not so good based on the outcome of the surgeries and the feedbacks from those who participated in the surgeries. Evaluations may be directed to different aspects related to a surgery including an evaluation on the surgery itself, such as the level of satisfaction from the medical team performing the surgery, the level of incident caused by or related to the setting, the degree of prolong due to a change in the surgery on the setup, the ration of the length of the surgery to the average length of the same type of surgery, etc. The evaluation may also be directed to the patients' recovery, including, e.g., speed attributed to the surgery performance, whether there are any after-surgery issues such as infection, etc. Such evaluations may be quantified numerically and may be combined to come up with an overall numerical score within a pre-determined range (e.g., 1-10). Such overall score without respect to the performance may serve, e.g., together with the categorical evaluations, as ground truth in the training data.

Figure 12:
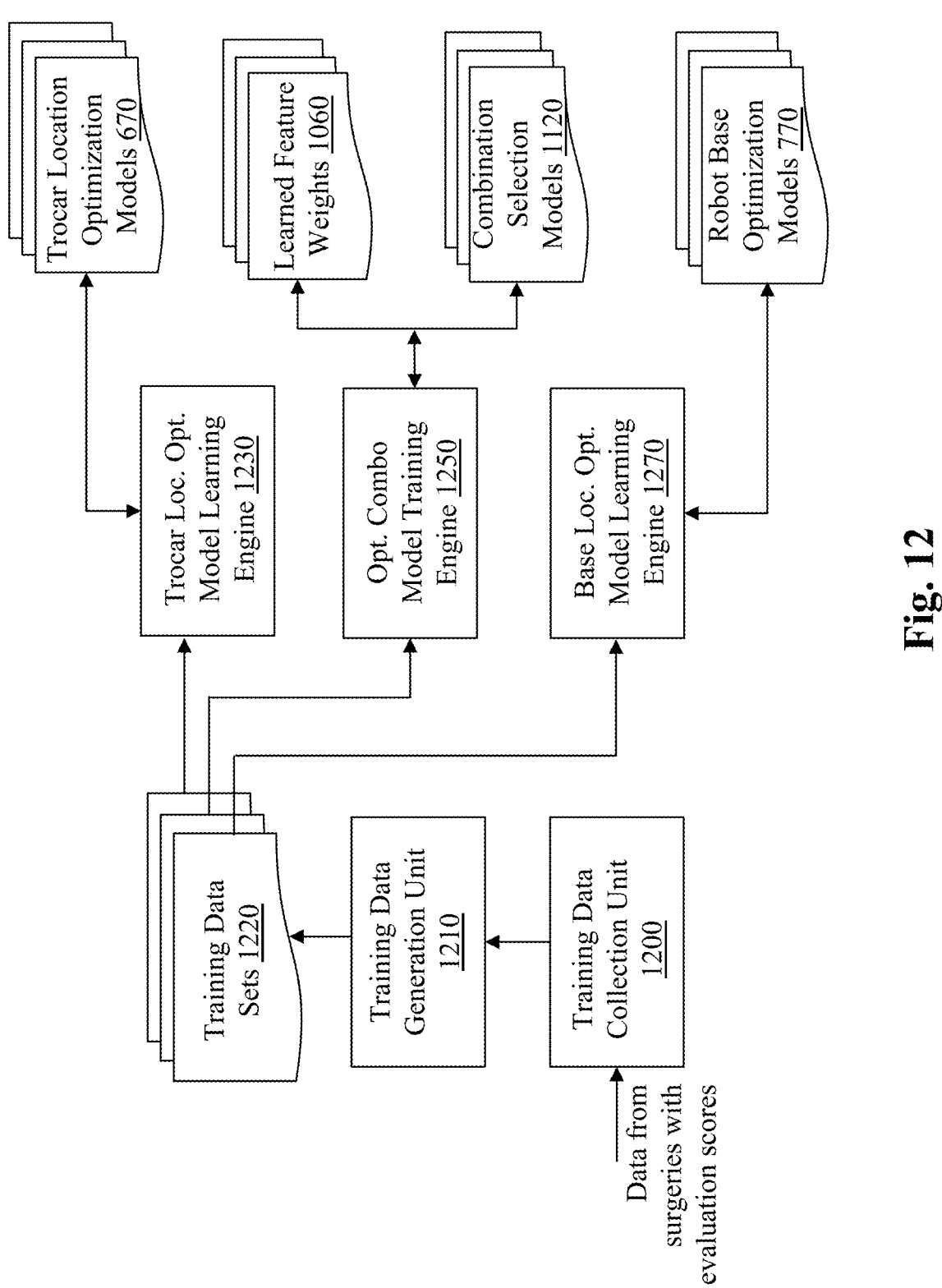
FIG. 12 depicts an exemplary high level system diagram for a machine learning mechanism to train different models used in sequential or simultaneous optimization of trocar/base locations, in accordance with an embodiment of the present teaching.

FIG. 12 depicts an exemplary high level system diagram for a machine learning mechanism to train different models used in sequential or simultaneous optimization of trocar/base locations, in accordance with an embodiment of the present teaching. In this exemplary embodiment, the machine learning mechanism as illustrated in FIG. 12 comprises a training data collection unit 1200, a training data generation unit 1210, and a training mechanism 1230. The training data so collected and generated (obtained appropriately based on the needs of the learning) may be used by the training mechanism 1230 in learning to produce trained models in 1240.

In this embodiment, the training mechanism 1230 may include multiple learning engines, each of which may be specialized to train a corresponding type of models. As illustrated in FIG. 12, the training mechanism 1230 includes a trocar location optimization model training engine 1230-1, a base location optimization model training engine 1230-3, and an optimal combination model training engine 1230-2. The trocar location optimization model training engine 1230-1 may be provided for deriving the trocar location optimization models 670 as used herein in sequential optimization mode. The base location optimization model training engine 1230-3 may be provided for deriving the trocar location optimization models 67 robot base optimization models 770 as used in sequential optimization model. The optimal combination model training engine 1230-2 may be provided for deriving the learned feature weights 1060 as used in simultaneous optimization scheme based on weighted sum solutions and the combination selection models 1120 in simultaneous optimization mode of operation.

Figure 13:
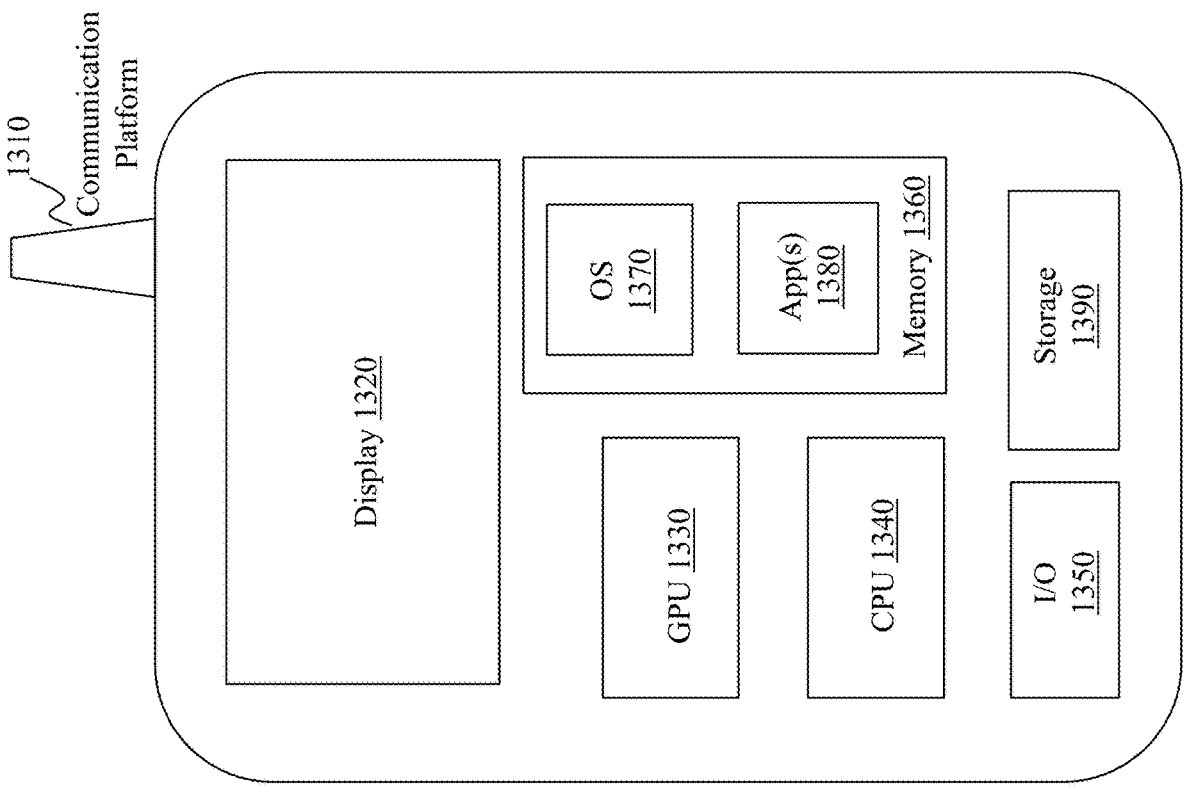
FIG. 13 is an illustrative diagram of an exemplary mobile device architecture that may be used to realize a specialized system implementing the present teaching in accordance with various embodiments.

FIG. 13 is an illustrative diagram of an exemplary mobile device architecture that may be used to realize a specialized system implementing the present teaching in accordance with various embodiments. In this example, the user device on which the present teaching may be implemented corresponds to a mobile device 1300, including, but not limited to, a smart phone, a tablet, a music player, a handled gaming console, a global positioning system (GPS) receiver, and a wearable computing device, or in any other form factor. Mobile device 1300 may include one or more central processing units ("CPUs") 1340, one or more graphic processing units ("GPUs") 1330, a display 1320, a memory 1360, a communication platform 1310, such as a wireless communication module, storage 1390, and one or more input/output (I/O) devices 1350. Any other suitable component, including but not limited to a system bus or a controller (not shown), may also be included in the mobile device 1300. As shown in FIG. 13, a mobile operating system 1370 (e.g., iOS, Android, Windows Phone, etc.), and one or more applications 1380 may be loaded into memory 1360 from storage 1390 in order to be executed by the CPU 1340. The applications 1380 may include a user interface or any other suitable mobile apps for information analytics and management according to the present teaching on, at least partially, the mobile device 1300. User interactions, if any, may be achieved via the I/O devices 1350 and provided to the various components connected via network(s).

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar with to adapt those technologies to appropriate settings as described herein. A computer with user interface elements may be used to implement a personal computer (PC) or other type of workstation or terminal device, although a computer may also act as a server if appropriately programmed. It is believed that those skilled in the art are familiar with the structure, programming, and general operation of such computer equipment and as a result the drawings should be self-explanatory.

Figure 14:
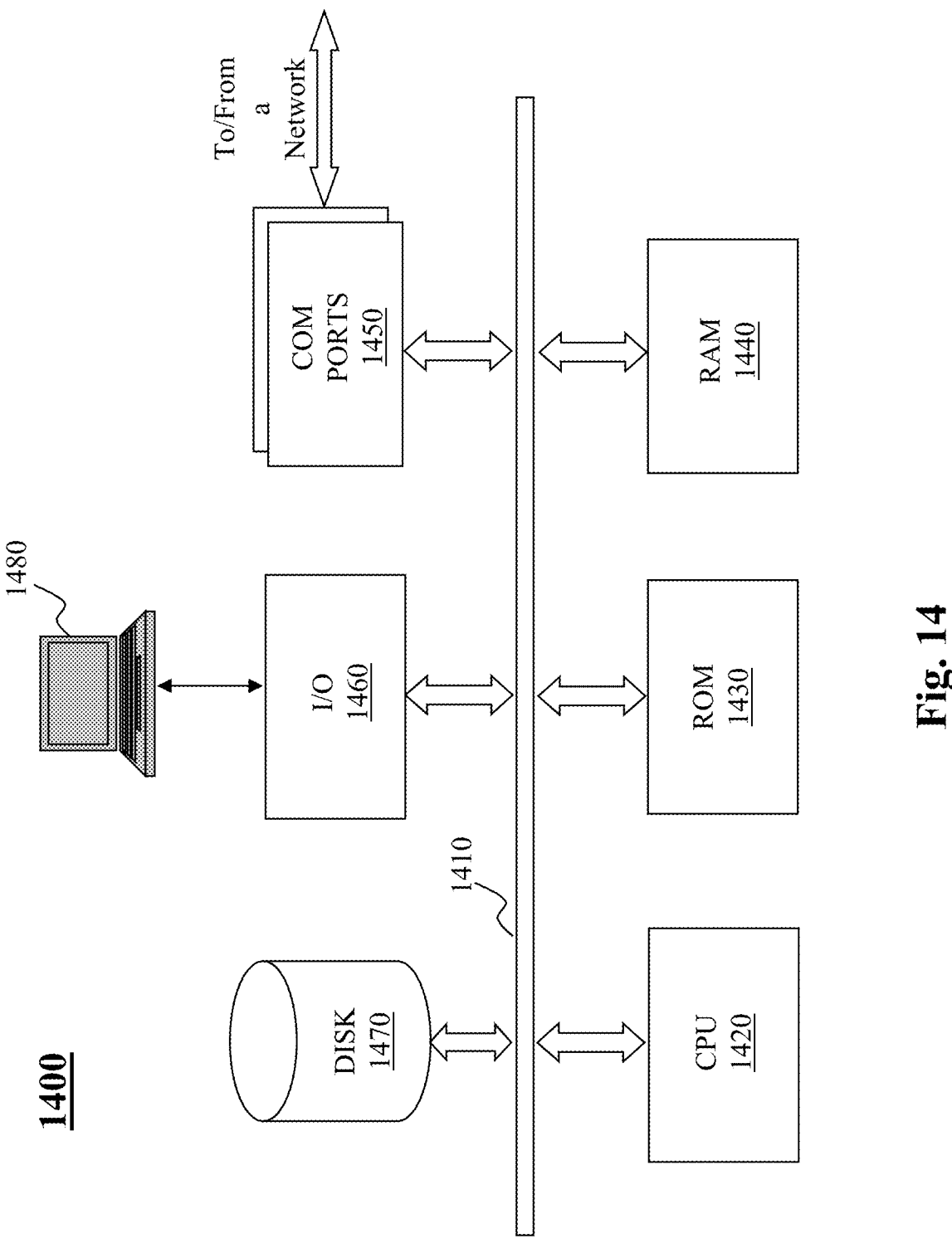
FIG. 14 is an illustrative diagram of an exemplary computing device architecture that may be used to realize a specialized system implementing the present teaching in accordance with various embodiments.

FIG. 14 is an illustrative diagram of an exemplary computing device architecture that may be used to realize a specialized system implementing the present teaching in accordance with various embodiments. Such a specialized system incorporating the present teaching has a functional block diagram illustration of a hardware platform, which includes user interface elements. The computer may be a general-purpose computer or a special purpose computer. Both can be used to implement a specialized system for the present teaching. This computer 800 may be used to implement any component or aspect of the framework as disclosed herein. For example, the information analytical and management method and system as disclosed herein may be implemented on a computer such as computer 1400, via its hardware, software program, firmware, or a combination thereof. Although only one such computer is shown, for convenience, the computer functions relating to the present teaching as described herein may be implemented in a distributed fashion on a number of similar platforms, to distribute the processing load.

Computer 1400, for example, includes COM ports 1450 connected to and from a network connected thereto to facilitate data communications. Computer 1400 also includes a central processing unit (CPU) 1420, in the form of one or more processors, for executing program instructions. The exemplary computer platform includes an internal communication bus 1410, program storage and data storage of different forms (e.g., disk 1470, read only memory (ROM) 1430, or random-access memory (RAM) 1440), for various data files to be processed and/or communicated by computer 1400, as well as possibly program instructions to be executed by CPU 1420. Computer 1400 also includes an I/O component 1460, supporting input/output flows between the computer and other components therein such as user interface elements 1480. Computer 1400 may also receive programming and data via network communications.

Hence, aspects of the methods of information analytics and management and/or other processes, as outlined above, may be embodied in programming. Program aspects of the technology may be thought of as "products" or "articles of manufacture" typically in the form of executable code and/or associated data that is carried on or embodied in a type of machine readable medium. Tangible non-transitory "storage" type media include any or all of the memory or other storage for the computers, processors or the like, or associated modules thereof, such as various semiconductor memories, tape drives, disk drives and the like, which may provide storage at any time for the software programming.

All or portions of the software may at times be communicated through a network such as the Internet or various other telecommunication networks. Such communications, for example, may enable loading of the software from one computer or processor into another, for example, in connection with information analytics and management. Thus, another type of media that may bear the software elements includes optical, electrical, and electromagnetic waves, such as used across physical interfaces between local devices, through wired and optical landline networks and over various air-links. The physical elements that carry such waves, such as wired or wireless links, optical links, or the like, also may be considered as media bearing the software. As used herein, unless restricted to tangible "storage" media, terms such as computer or machine "readable medium" refer to any medium that participates in providing instructions to a processor for execution.

Hence, a machine-readable medium may take many forms, including but not limited to, a tangible storage medium, a carrier wave medium or physical transmission medium. Non-volatile storage media include, for example, optical or magnetic disks, such as any of the storage devices in any computer(s) or the like, which may be used to implement the system or any of its components as shown in the drawings. Volatile storage media include dynamic memory, such as a main memory of such a computer platform. Tangible transmission media include coaxial cables; copper wire and fiber optics, including the wires that form a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a physical processor for execution.

Those skilled in the art will recognize that the present teachings are amenable to a variety of modifications and/or enhancements. For example, although the implementation of various components described above may be embodied in a hardware device, it may also be implemented as a software only solution, e.g., an installation on an existing server. In addition, the techniques as disclosed herein may be implemented as a firmware, firmware/software combination, firmware/hardware combination, or a hardware/firmware/software combination.

While the foregoing has described what are considered to constitute the present teachings and/or other examples, it is understood that various modifications may be made thereto and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

We claim:

1. A method implemented on at least one processor, a memory, and a communication platform, comprising:

obtaining an instrument access map of a surgical instrument for performing a surgical operation on an organ, wherein the instrument access map defines a surface area on the organ with a plurality of cut points therein representing a surgery trajectory;

obtaining information related to a robot to be deployed for controlling the surgical instrument to perform the surgical operation along the surgery trajectory and a surgical environment where the surgical operation is to be performed;

generating, based on the information, a robot access map comprising one or more robot base locations, from where the robot is to be deployed to control the surgical instrument to reach the instrument access map;

selecting, from the robot access map, one of the robot base locations based on evaluation parameters determined with respect to each of the robot base locations, wherein the selecting further comprises:

obtaining, with respect to each of the robot base locations, an assessment in terms of a set of evaluation parameters; and determining the selected robot base location based on the evaluation parameters obtained for each of the robot base locations in the robot access map; and generating control signals for automatically configuring deployment of the robot at the selected robot base location to facilitate the surgical operation.

2. The method of claim 1, wherein the information comprises at least one of:

a dimension of the robot;

kinematic parameters associated with the robot;

spatial information related to the surgical environment; and a resolution to be used to determine the one or more robot base locations.

3. The method of claim 2, wherein the step of generating the robot access map comprises:

deriving multiple candidate robot base locations based on the spatial information of the surgical environment and the resolution;

determining, with respect to each of the candidate robot base locations, whether the robot is able to control the surgical instrument to reach the instrument access map based on kinematic feasibility of the robot determined based on the kinematic parameters; and creating the robot access map by merging those of the candidate robot base locations from where the robot is able to control the surgical instrument to reach the entire instrument access map.

4. The method of claim 3, wherein an ability of the surgical instrument to reach the instrument access map indicates that a tip of the surgical instrument is able to reach the plurality of cut points included in the instrument access map.

5. The method of claim 1, wherein the set of evaluation parameters includes at least one of:

an actual access map specifying a sub-area in the instrument access map that the robot deployed at the robot base location is able to control the surgical instrument to reach;

a coverage indicating a portion of the instrument access map that overlaps with the actual access map;

a distance from the robot base location to a location of the surgical instrument;

an angle between a surface norm at the location of the surgical instrument and a line formed between the robot at the robot base location and the location of the surgical instrument; and a proximity to singularity of the robot determined based on kinematic parameter configurations needed for the robot to control the surgical instrument to reach the plurality of cut points.

6. The method of claim 1, wherein the step of determining the selected robot base location is based on a robot base location optimization model obtained via machine learning based on training data collected from past historic surgery data.

7. Machine readable and non-transitory medium having information recorded thereon, wherein the information, when read by the machine, causes the machine to perform the following steps:

obtaining an instrument access map of a surgical instrument for performing a surgical operation on an organ, wherein the instrument access map defines a surface area on the organ with a plurality of cut points therein representing a surgery trajectory;

obtaining information related to a robot to be deployed for controlling the surgical instrument to perform the surgical operation along the surgery trajectory and a surgical environment where the surgical operation is to be performed;

generating, based on the information, a robot access map comprising one or more robot base locations, from where the robot is to be deployed to control the surgical instrument to reach the instrument access map;

selecting, from the robot access map, one of the robot base locations based on evaluation parameters determined with respect to each of the robot base locations, wherein the selecting further comprises:

obtaining, with respect to each of the robot base locations, an assessment in terms of a set of evaluation parameters; and determining the selected robot base location based on the evaluation parameters obtained for each of the robot base locations in the robot access map; and generating control signals for automatically configuring deployment of the robot at the selected robot base location to facilitate the surgical operation.

8. The medium of claim 7, wherein the information comprises at least one of:

a dimension of the robot;

kinematic parameters associated with the robot;

spatial information related to the surgical environment; and a resolution to be used to determine the one or more robot base locations.

9. The medium of claim 8, wherein the step of generating the robot access map comprises:

deriving multiple candidate robot base locations based on the spatial information of the surgical environment and the resolution;

determining, with respect to each of the candidate robot base locations, whether the robot is able to control the surgical instrument to reach the instrument access map based on kinematic feasibility of the robot determined based on the kinematic parameters; and creating the robot access map by merging those of the candidate robot base locations from where the robot is able to control the surgical instrument to reach the entire instrument access map.

10. The medium of claim 9, wherein an ability of the surgical instrument to reach the instrument access map indicates that a tip of the surgical instrument is able to reach the plurality of cut points included in the instrument access map.

11. The medium of claim 7, wherein the set of evaluation parameters includes at least one of:

an actual access map specifying a sub-area in the instrument access map that the robot deployed at the robot base location is able to control the surgical instrument to reach;

a coverage indicating a portion of the instrument access map that overlaps with the actual access map;

a distance from the robot base location to a location of the surgical instrument;

an angle between a surface norm at the location of the surgical instrument and a line formed between the robot at the robot base location and the location of the surgical instrument; and a proximity to singularity of the robot determined based on kinematic parameter configurations needed for the robot to control the surgical instrument to reach the plurality of cut points.

12. The medium of claim 7, wherein the step of determining the selected robot base location is based on a robot base location optimization model obtained via machine learning based on training data collected from past historic surgery data.

13. A system, comprising a robot base location optimizer, implemented by a processor and configured for:

obtaining an instrument access map of a surgical instrument for performing a surgical operation on an organ, wherein the instrument access map defines a surface area on the organ with a plurality of cut points therein representing a surgery trajectory;

obtaining information related to a robot to be deployed for controlling the surgical instrument to perform the surgical operation along the surgery trajectory and a surgical environment where the surgical operation is to be performed;

generating, based on the information, a robot access map comprising one or more robot base locations, from where the robot is to be deployed to control the surgical instrument to reach the instrument access map;

selecting, from the robot access map, one of the robot base locations based on evaluation parameters determined with respect to each of the robot base locations, wherein the selecting further comprises:

obtaining, with respect to each of the robot base locations, an assessment in terms of a set of evaluation parameters; and determining the selected robot base location based on the evaluation parameters obtained for each of the robot base locations in the robot access map; and generating control signals for automatically configuring deployment of the robot at the selected robot base location to facilitate the surgical operation.

14. The system of claim 13, wherein the information comprises at least one of:

a dimension of the robot;

kinematic parameters associated with the robot;

spatial information related to the surgical environment; and a resolution to be used to determine the one or more robot base locations.

15. The system of claim 14, wherein the step of generating the robot access map comprises:

deriving multiple candidate robot base locations based on the spatial information of the surgical environment and the resolution;

determining, with respect to each of the candidate robot base locations, whether the robot is able to control the surgical instrument to reach the instrument access map based on kinematic feasibility of the robot determined based on the kinematic parameters; and creating the robot access map by merging those of the candidate robot base locations from where the robot is able to control the surgical instrument to reach the entire instrument access map.

16. The system of claim 15, wherein an ability of the surgical instrument to reach the instrument access map indicates that a tip of the surgical instrument is able to reach the plurality of cut points included in the instrument access map.

17. The system of claim 13, wherein the set of evaluation parameters includes at least one of:

an actual access map specifying a sub-area in the instrument access map that the robot deployed at the robot base location is able to control the surgical instrument to reach;

a coverage indicating a portion of the instrument access map that overlaps with the actual access map;

a distance from the robot base location to a location of the surgical instrument;

an angle between a surface norm at the location of the surgical instrument and a line formed between the robot at the robot base location and the location of the surgical instrument; and a proximity to singularity of the robot determined based on kinematic parameter configurations needed for the robot to control the surgical instrument to reach the plurality of cut points.

18. The system of claim 13, wherein the step of determining the selected robot base location is based on a robot base location optimization model obtained via machine learning based on training data collected from past historic surgery data.

* * * * *